United States Patent
Kawanishi

(10) Patent No.: US 10,271,814 B2
(45) Date of Patent: Apr. 30, 2019

(54) CONTROL APPARATUS, OPERATION METHOD FOR CONTROL APPARATUS, AND STORAGE MEDIUM

(71) Applicant: CANON KABUSHIKI KAISHA, Tokyo (JP)

(72) Inventor: Tomohiro Kawanishi, Tachikawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 438 days.

(21) Appl. No.: 15/091,738

(22) Filed: Apr. 6, 2016

(65) Prior Publication Data

US 2016/0213347 A1    Jul. 28, 2016

Related U.S. Application Data

(63) Continuation of application No. PCT/JP2014/005211, filed on Oct. 15, 2014.

(30) Foreign Application Priority Data

Oct. 30, 2013    (JP) .................................. 2013-225823

(51) Int. Cl.
*A61B 6/00*    (2006.01)

(52) U.S. Cl.
CPC .............. *A61B 6/54* (2013.01); *A61B 6/4464* (2013.01); *A61B 6/462* (2013.01); *A61B 6/465* (2013.01); *A61B 6/467* (2013.01)

(58) Field of Classification Search
CPC ....... A61B 6/4464; A61B 6/462; A61B 6/465; A61B 6/467; A61B 6/54
See application file for complete search history.

(56) References Cited

U.S. PATENT DOCUMENTS

2011/0057111 A1*   3/2011   Nishino .................... G01T 7/00
                                                                250/370.08

FOREIGN PATENT DOCUMENTS

| JP | 2000-166908 | 6/2000 |
|---|---|---|
| JP | 2003-284709 | 10/2003 |
| JP | 2003-290200 | 10/2003 |
| JP | 2007-050075 | 3/2007 |
| JP | 2007-275261 | 10/2007 |
| JP | 2009-219586 | 1/2009 |
| JP | 2010-110433 | 5/2010 |
| JP | 2010-220817 | 10/2010 |
| JP | 2011-072775 | 4/2011 |
| JP | 2013-052016 | 3/2013 |

OTHER PUBLICATIONS

Translation of JP 2010-110433 published 2010.*
Translation of JP 2007-050075 published 2007.*
Translation of JP 2013-052016 published 2013.*
Translation of JP 2007-275261 published 2007.*

* cited by examiner

*Primary Examiner* — Chih-Cheng Kao
(74) *Attorney, Agent, or Firm* — Venable LLP

(57) ABSTRACT

A control apparatus includes a changing unit which changes the sequence of a plurality of imaging examination information, based on a user operation, displayed based on an imaging sequence on an imaging control screen, and a control unit which controls at least one of a radiation detector and a radiation generation unit which are associated with imaging examination information as an imaging target based on the sequence changed by the changing unit.

15 Claims, 22 Drawing Sheets

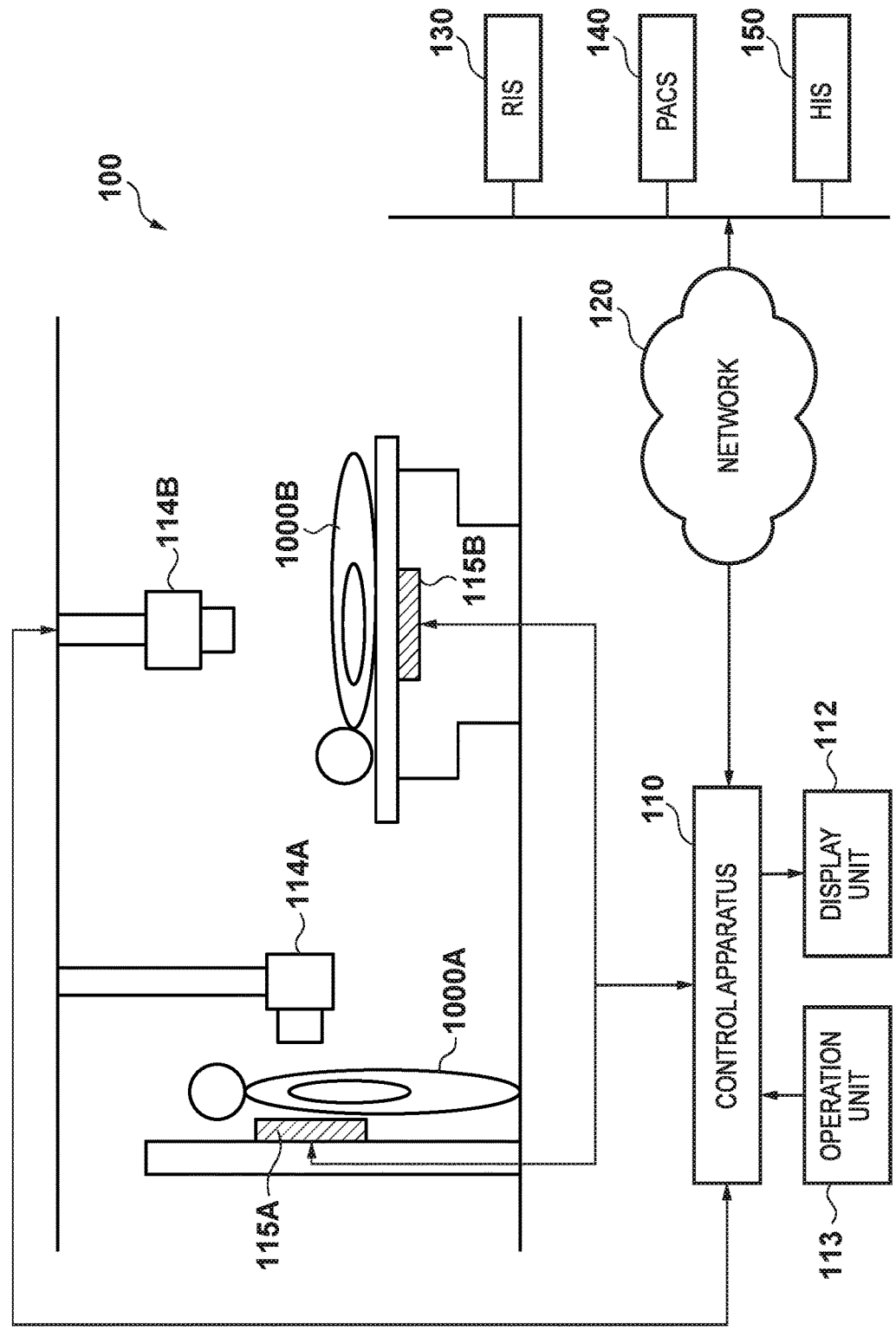

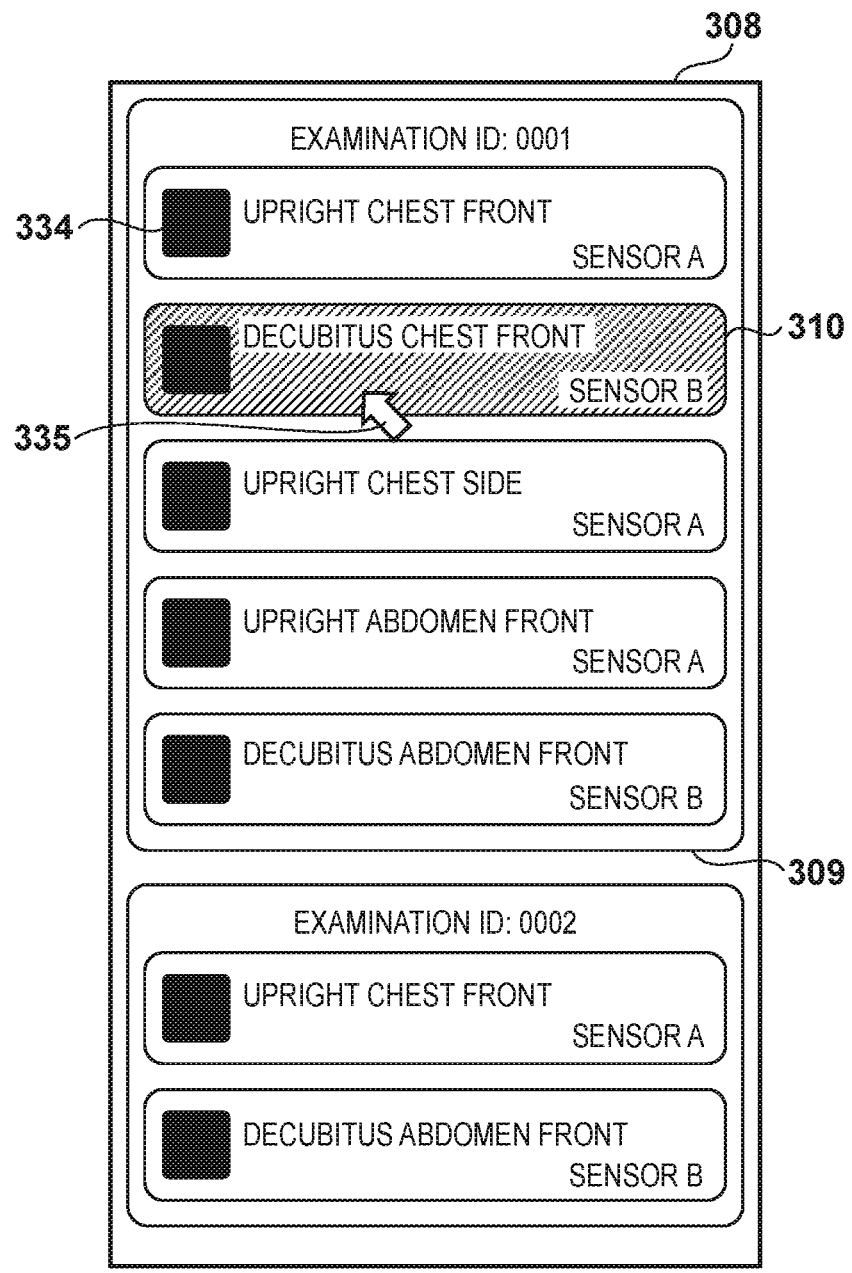

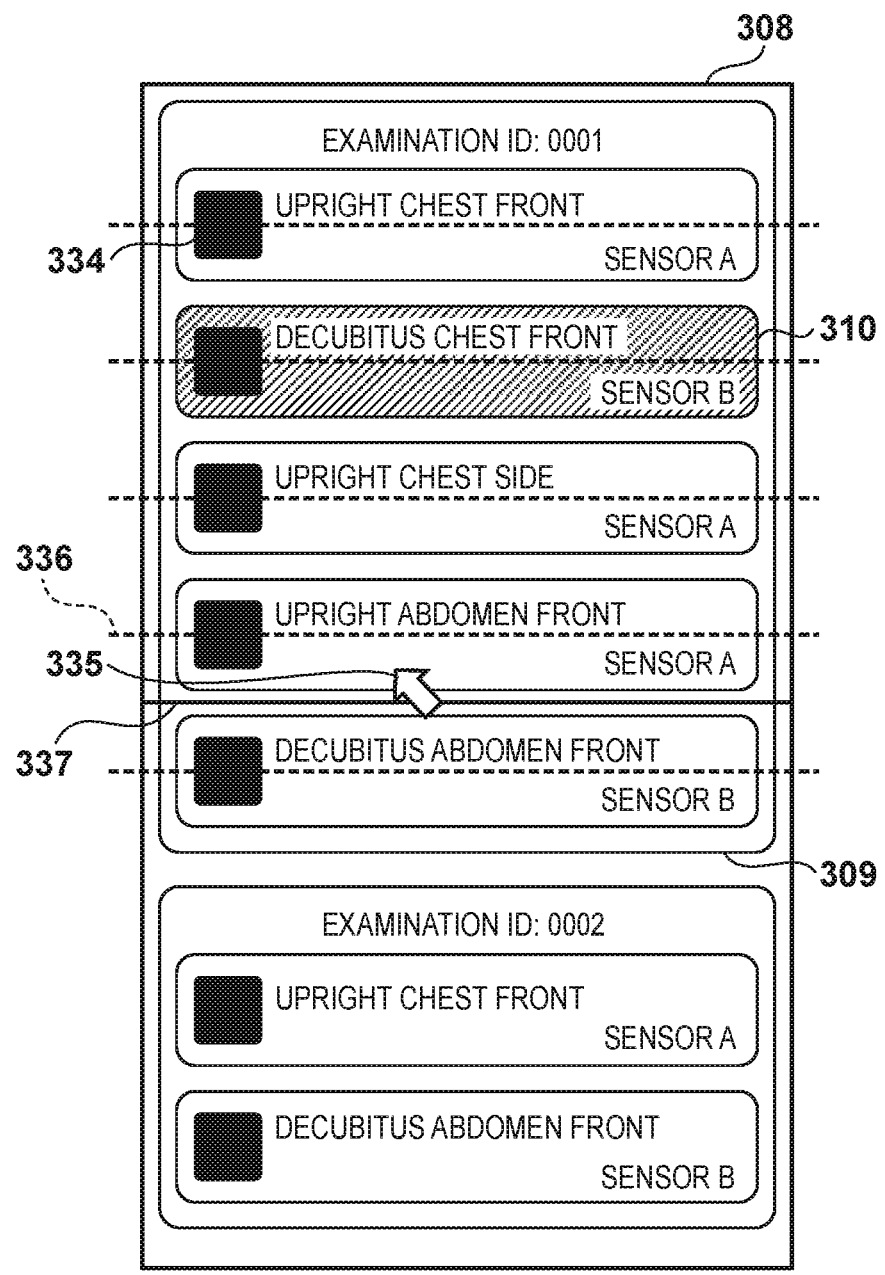

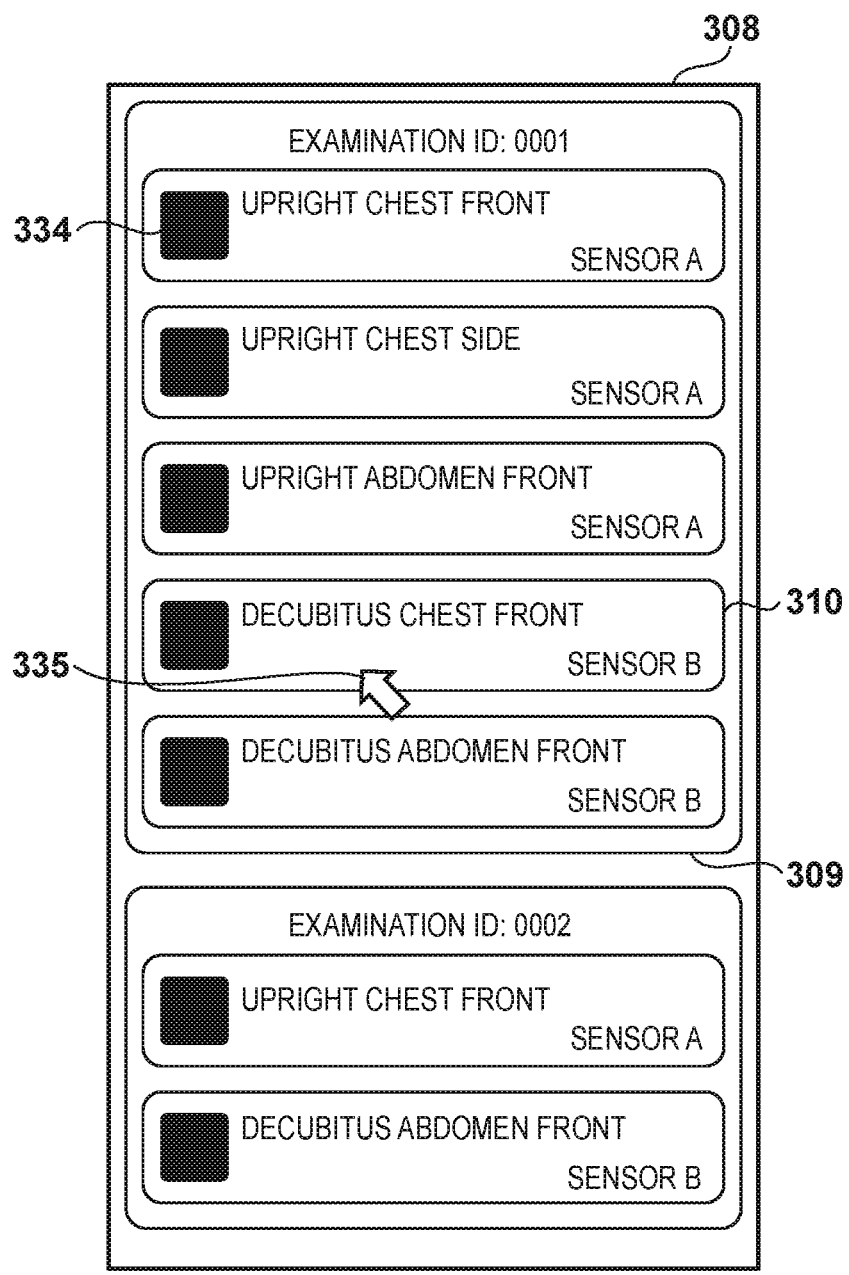
FIG. 3B-C

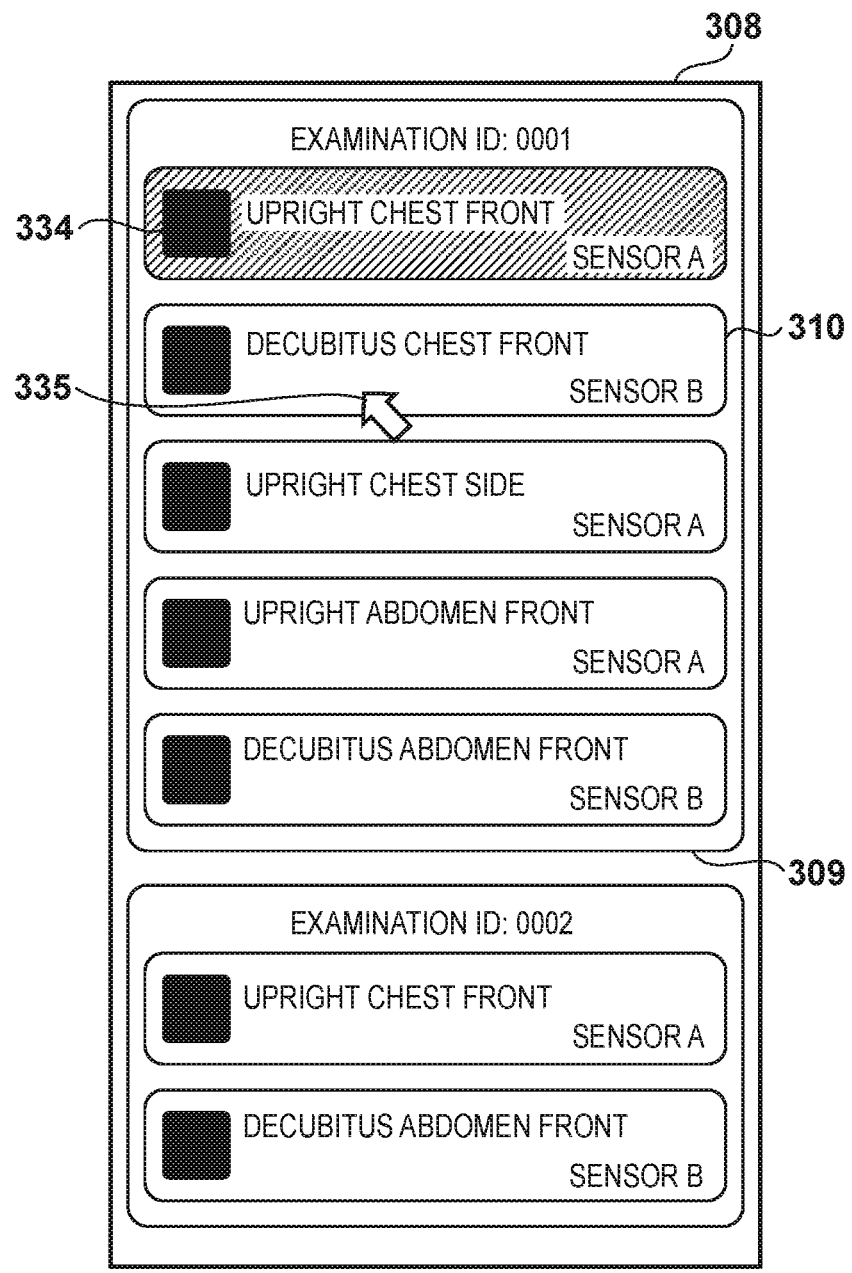

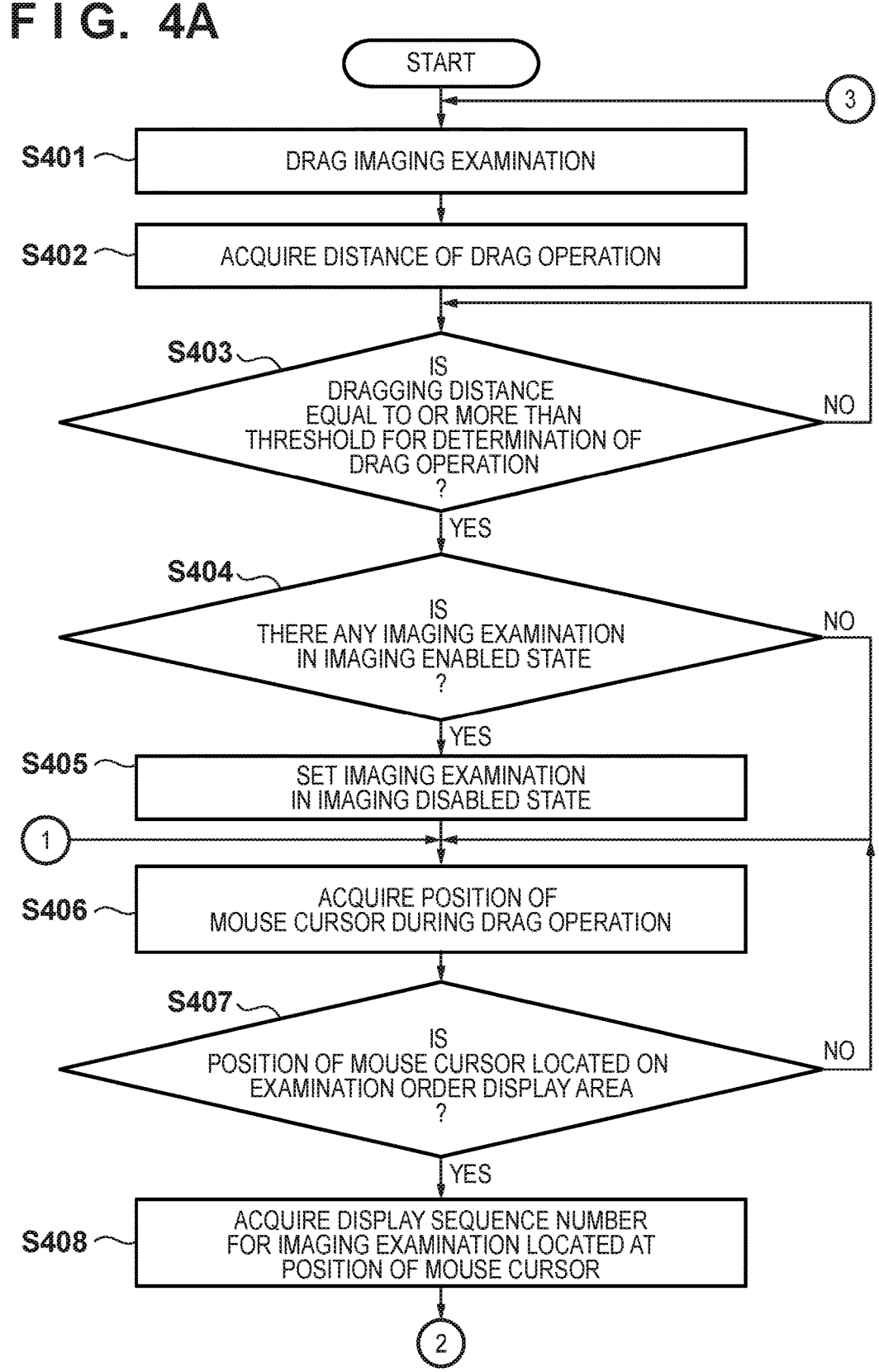

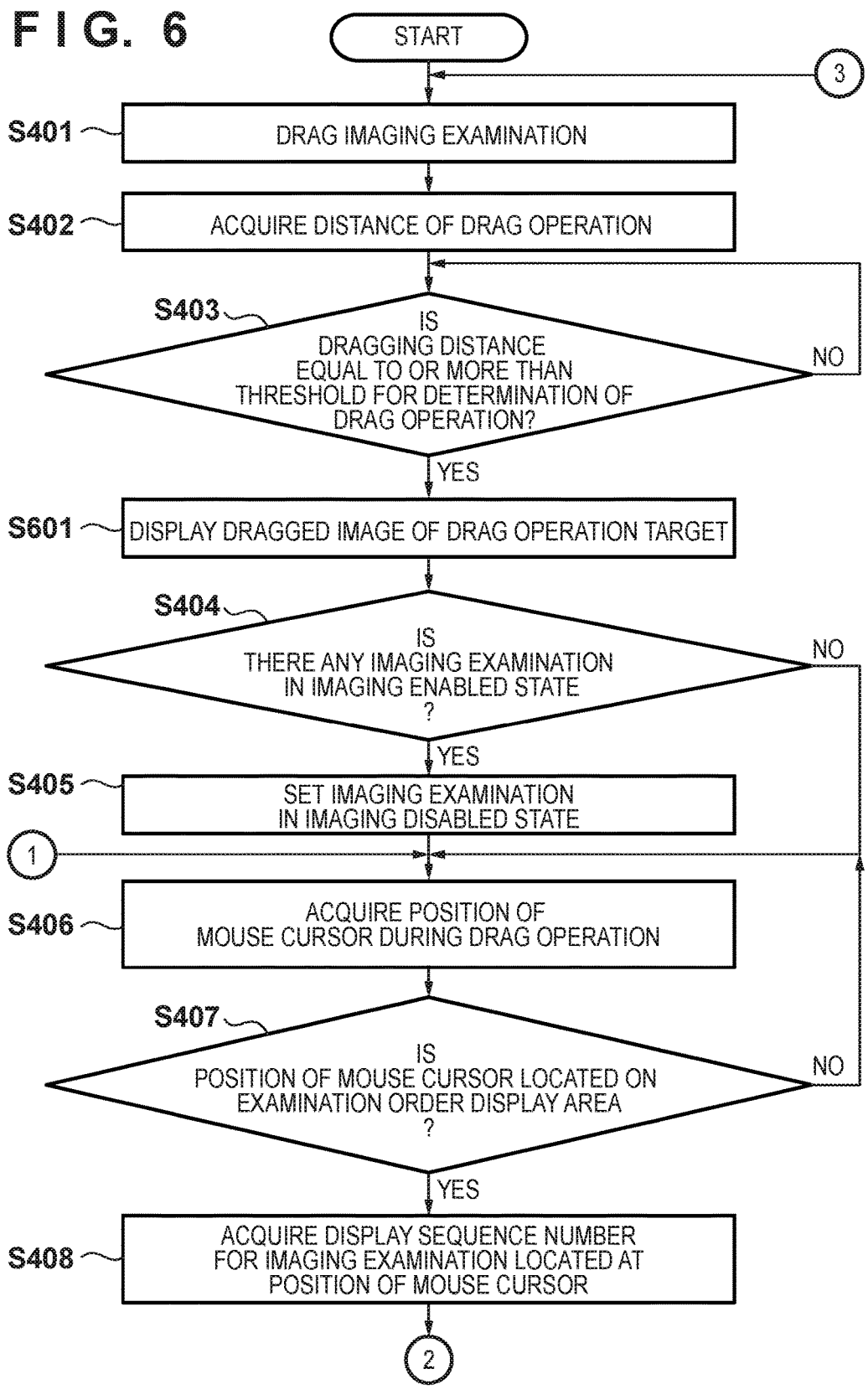

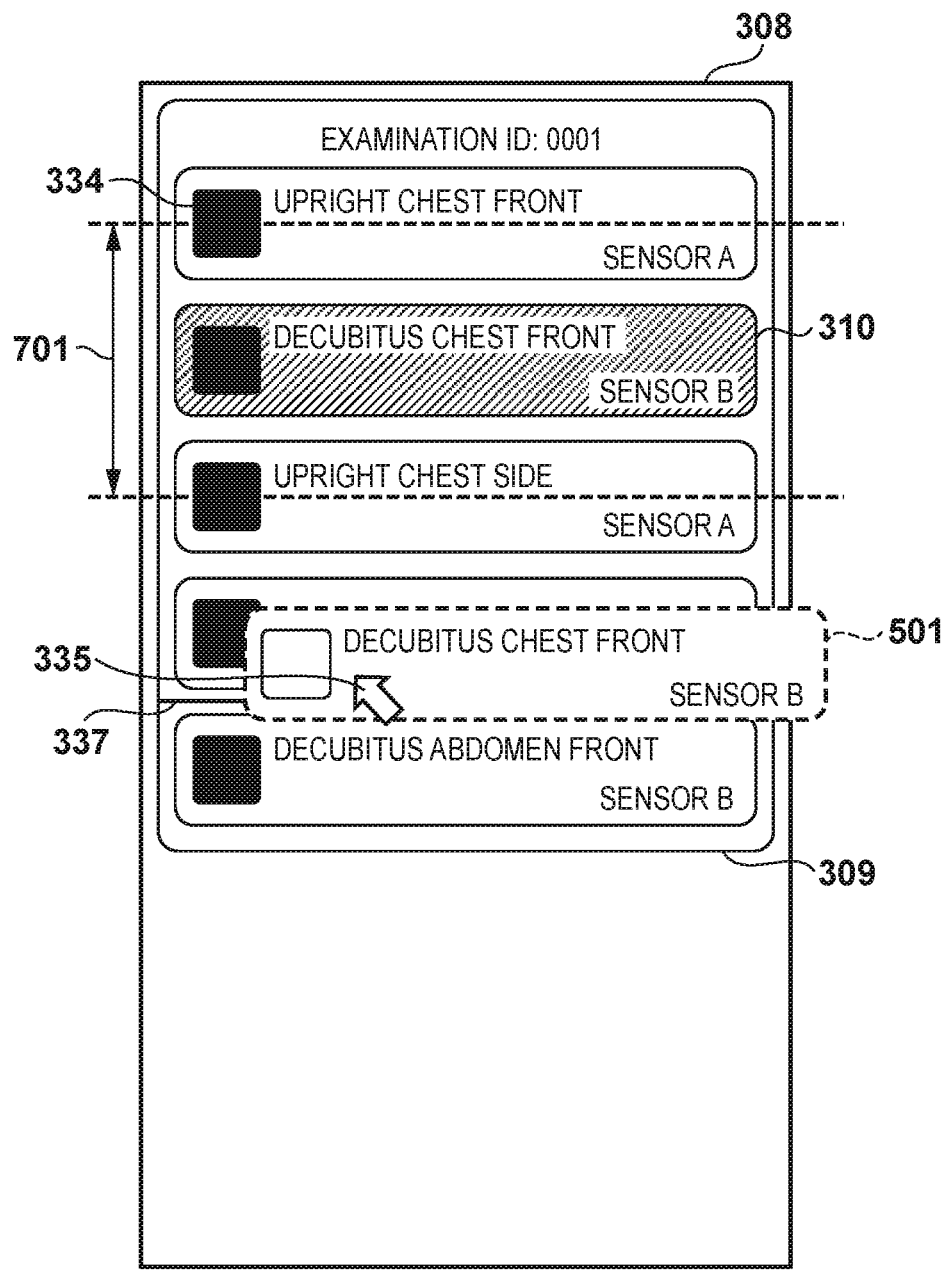

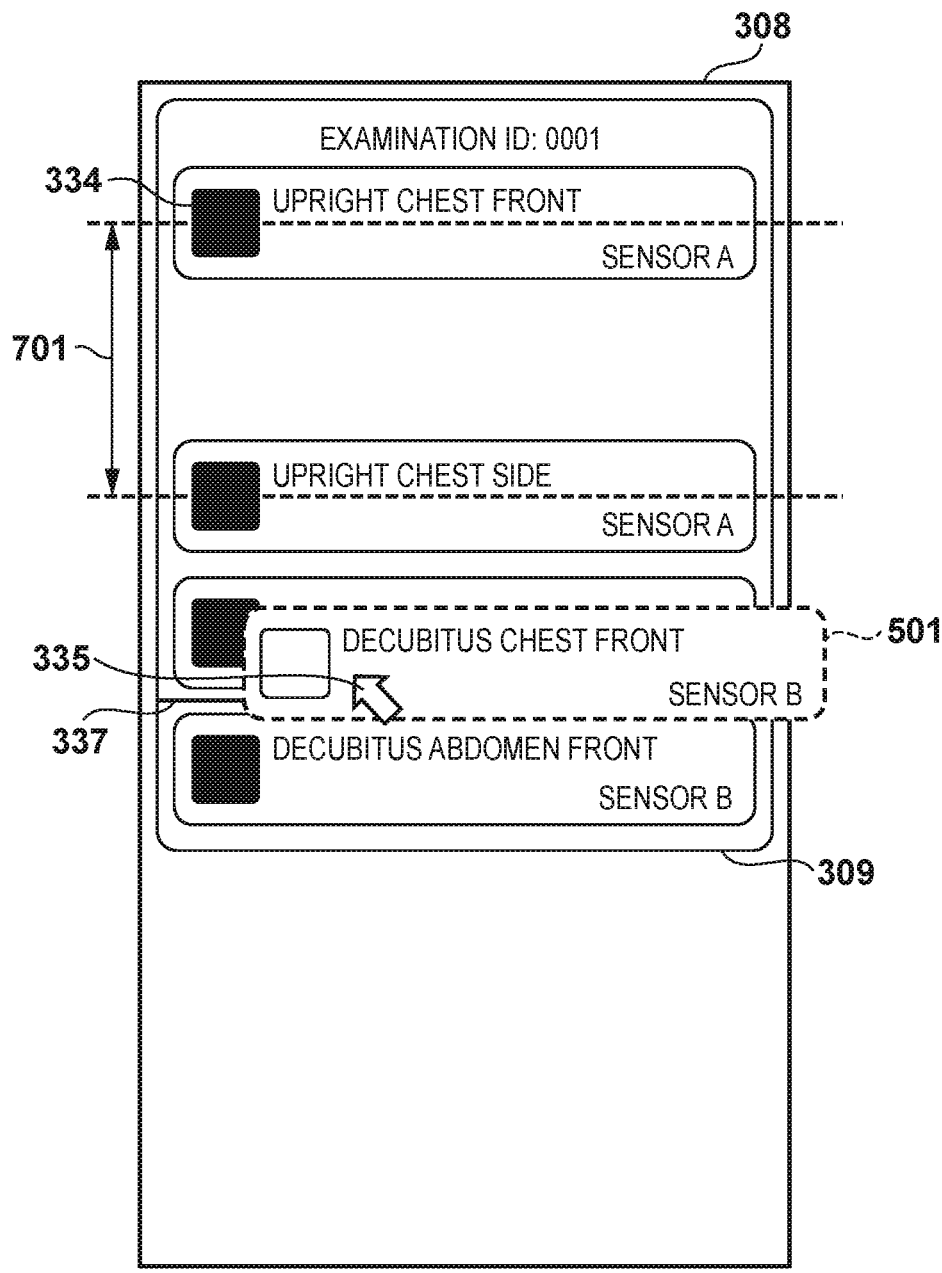

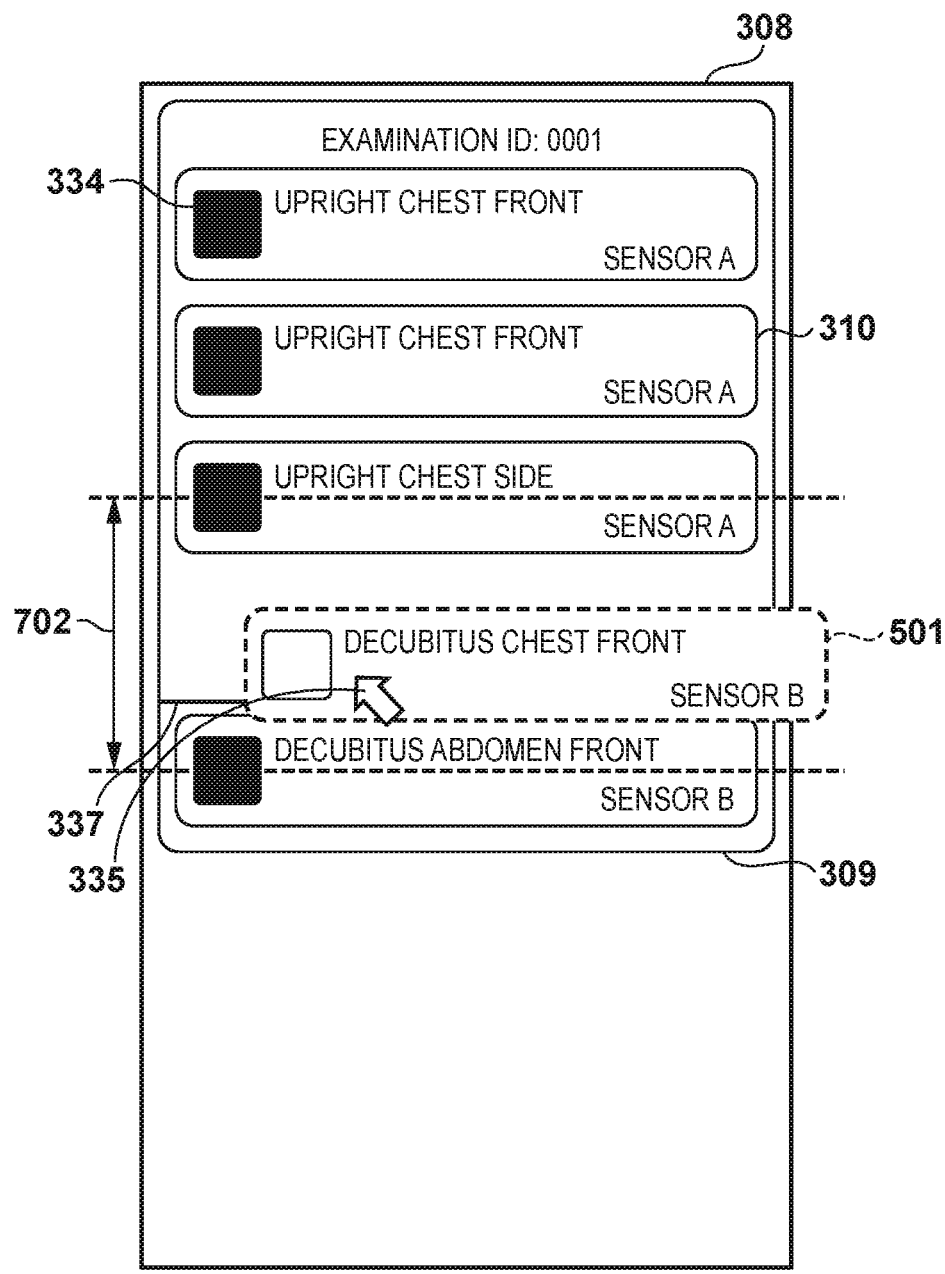

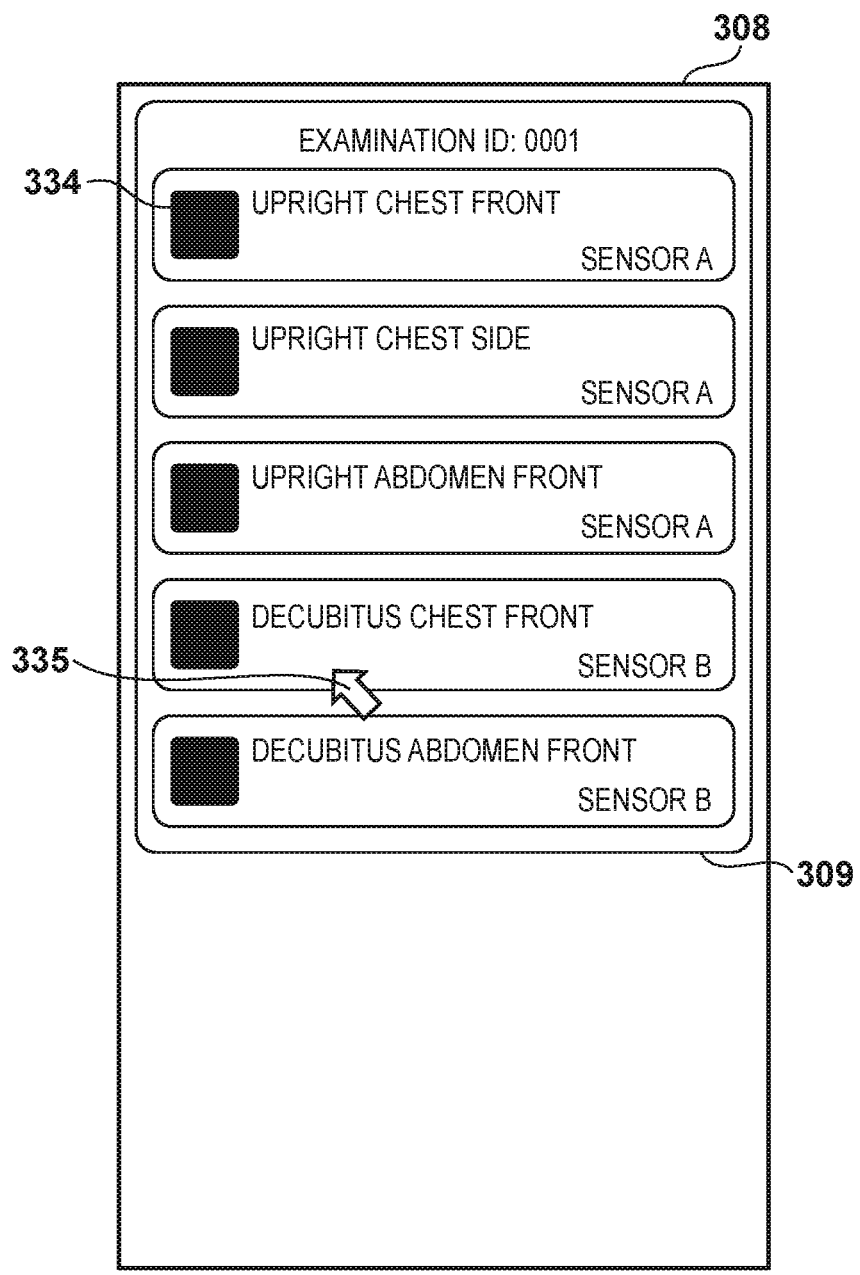

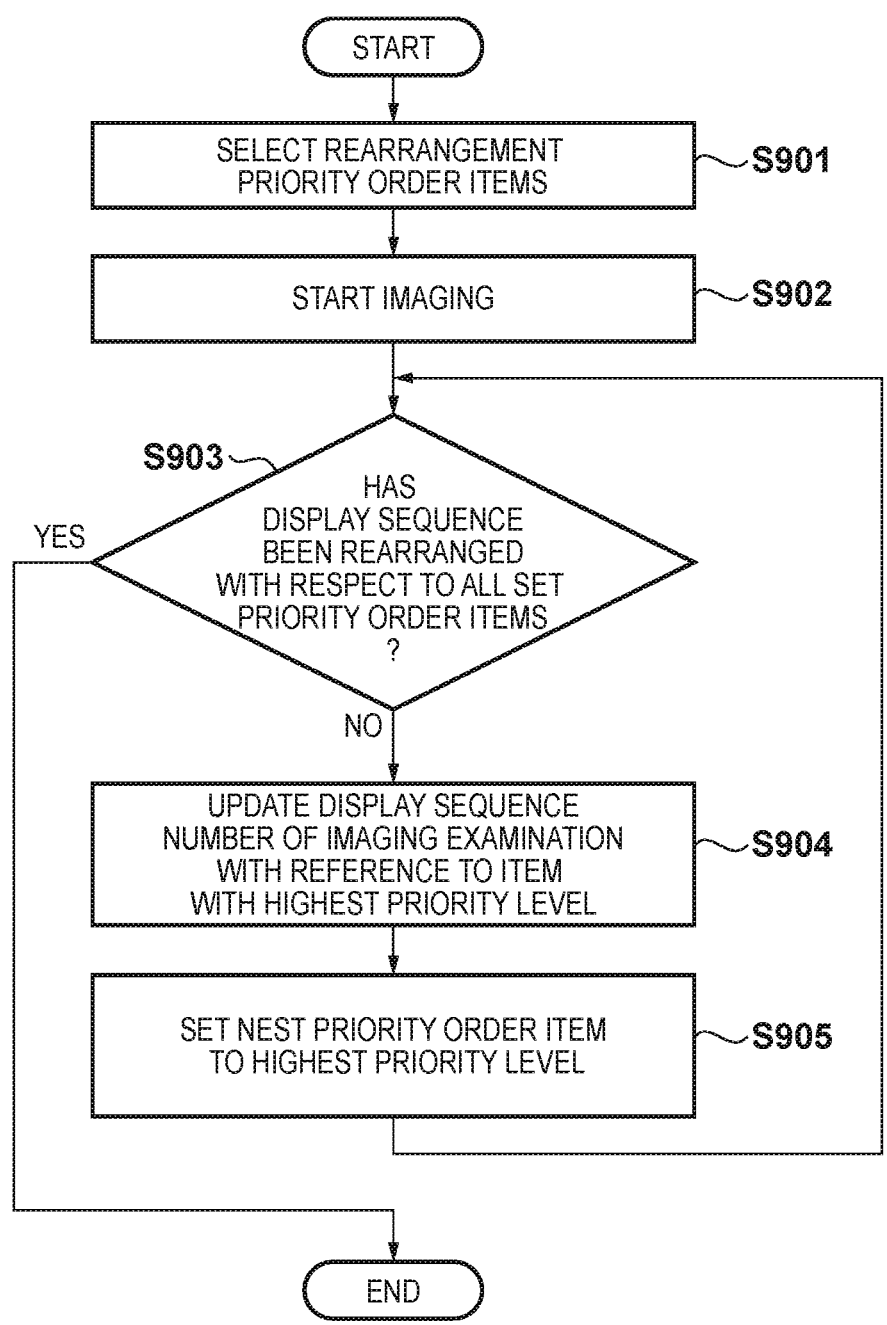

CONTROL APPARATUS, OPERATION METHOD FOR CONTROL APPARATUS, AND STORAGE MEDIUM

This application is a continuation of International Patent Application No. PCT/JP2014/005211 filed on Oct. 15, 2014, and claims priority to Japanese Patent Application No. 2013-225823 filed on Oct. 30, 2013, the entire content of both of which is incorporated herein by reference.

TECHNICAL FIELD

The present invention relates to a control apparatus, an operation method for the control apparatus, and a storage medium and, more particularly, to a technique of controlling the operations of a radiation detector and a radiation generation unit.

BACKGROUND ART

Conventionally, in the medical field, a radiation image (an X-ray image using X-rays, in particular) is obtained by irradiating an object with radiation and making a radiation detector detect the intensity of transmitted radiation. In general, a network is constructed in a hospital and various medical apparatuses are connected to the network and cooperate with an HIS (Hospital Information System), an RIS (Radiology Information System), a medical image server, and the like.

In general, when using a radiation imaging apparatus in a hospital, a doctor sends an examination order which designates an examination region of a subject and the like to an examination technician who operates the radiation imaging apparatus. The examination order includes imaging examination information including different combinations of the imaging postures of the subject, imaging regions, imaging directions, and the like, which are necessary for the examination. An examination order is directly and manually input to the radiation imaging apparatus by the examination technician (operator) or automatically input to the radiation imaging apparatus via network such an HIS or RIS.

Assume that an examination order is input via an HIS, which designates imaging of a given patient in the order of "1. upright chest front", "2. decubitus chest front", "3. upright chest side", and "4. decubitus chest side". A doctor who inputs an examination order generally inputs an examination order based on the sequence of interpreting radiation images. For this reason, the sequence designated by the order sometimes differs from the sequence which facilitates imaging performed by the examination technician. Executing radiation imaging in accordance with the sequence designated by an examination order input by the doctor sometimes forces a patient to change his/her posture for each imaging operation, thereby increasing the burden on the patient.

Under this circumstance, PTL 1 discloses an examination system which changes an imaging sequence based on a predetermined conversion table before imaging.

CITATION LIST

Patent Literature

PTL 1: Japanese Patent Laid-Open No. 2000-166908

SUMMARY OF INVENTION

Technical Problem

A proper imaging sequence, however, sometimes changes depending on the situation in a site where imaging is performed, for example, the examination technician, the imaging environment, or the physical condition of the patient. Assume that in such a case, each examination technician temporarily interrupts imaging depending on the situation, and changes the imaging sequence upon returning to the screen before imaging. In this case, such an operation increases the time and effort spent by the examination technician, resulting in a deterioration in imaging efficiency.

In addition, as an imaging sequence is changed and imaging examination information for the next imaging operation is changed, it is necessary to control a radiation detector and a radiation generator. It takes much time and effort to manually perform such an operation. Besides, the operator sometimes performs an unnecessary operation, resulting in a deterioration in imaging efficiency.

The present invention has been made in consideration of the above problems and has as its object to enable efficient imaging in an imaging sequence according to the intention of the operator.

Solution to Problem

A control apparatus according to the present invention which achieves the above object is a control apparatus comprising: a changing unit configured to change a sequence of a plurality of imaging examination information, based on a user operation, displayed based on an imaging sequence on an imaging control screen; and a control unit configured to control at least one of a radiation detector and a radiation generation unit which are associated with imaging examination information as an imaging target based on the sequence changed by the changing unit.

Advantageous Effects of Invention

The present invention enables efficient imaging in an imaging sequence according to the intention of the operator.

Further features of the present invention will become apparent from the following description of exemplary embodiments (with reference to the attached drawings).

BRIEF DESCRIPTION OF DRAWINGS

The accompanying drawings, which are incorporated in and constitute a part of the specification, illustrate embodiments of the invention and, together with the description, serve to explain the principles of the invention.

FIG. 1 is a view showing the schematic arrangement of a radiation imaging system according to an embodiment of the present invention;

FIGS. 3B-A, 3B-B, 3B-C, and 3B-D are views each showing how a display sequence is changed on an imaging screen by a drag-and-drop operation according to the embodiment of the present invention;

FIGS. 4A and 4B are flowcharts each showing a processing procedure by which the control apparatus according to the embodiment of the present invention changes a display sequence in accordance with a drag-and-drop operation;

FIG. 6 is a flowchart showing a processing procedure by which the control apparatus according to the embodiment of the present invention changes the display sequence of imaging examination information;

FIGS. 7A to 7D are views each showing how the sequence of imaging examination information is rearranged by dragging imaging examination information with the mouse cursor according to the embodiment of the present invention;

FIG. 9 is a flowchart showing a processing procedure by which a control apparatus according to the second embodiment of the present invention changes the display sequence of imaging examination information in accordance with preset priority order items;

DESCRIPTION OF EMBODIMENTS

Figure 2A:
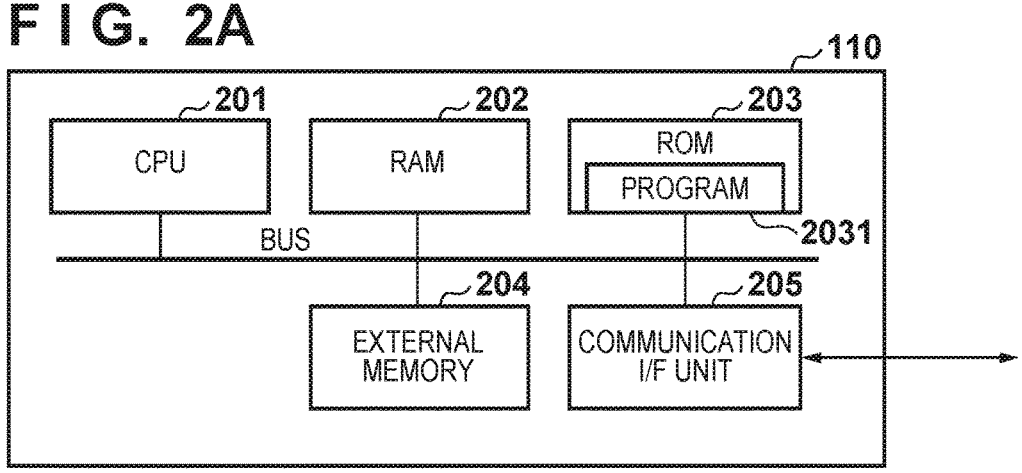
FIG. 2A is a schematic view showing an example of the hardware arrangement of a control apparatus according to the embodiment of the present invention.

The embodiments of the present invention will be described below with reference to the accompanying drawings.

First Embodiment

1. Schematic Arrangement of Radiation Imaging System

FIG. 1 is a schematic view showing an example of the schematic arrangement of a radiation imaging system 100 according to an embodiment of the present invention. The radiation imaging system 100 includes a control apparatus 110, radiation generation units 114A and 114B, radiation detectors 115A and 115B, an RIS (Radiology Information System) 130, an image server (PACS) 140, and an HIS (Hospital Information System) 150.

The control apparatus 110 is wiredly or wirelessly connected to a display unit 112, an operation unit 113, the radiation generation units 114A and 114B, and the radiation detectors 115A and 115B, and controls their operations. The control apparatus 110 is also connected to the RIS (Radiology Information System) 130, the image server (PACS) 140, and the HIS (Hospital Information System) 150 via a network 120, and hence can exchange radiation images, patient information, and the like with them.

The display unit 112 displays imaging examination information, obtained radiation images, various types of information, and the like. The operation unit 113 receives input information from the operator. In this embodiment, the display unit 112 is a monitor, and the operation unit 113 includes a keyboard and a mouse.

The radiation generation units 114A and 114B include radiation tubes which generate radiation, and irradiate patients 1000A and 1000B with radiation. The patient 1000A is an upright position, and the patient 1000B is in a decubitus position. The radiation generation units 114A and 114B and the radiation detectors 115A and 115B are arranged at positions suitable for imaging.

The radiation detectors 115A and 115B respectively detect radiation applied from the radiation generation units 114A and 114B. The control apparatus 110 performs image processing for radiation image data detected and obtained by the radiation detectors 115A and 115B, and displays the resultant data as radiation images on the display unit 112.

Although this embodiment will exemplify the radiation imaging system 100 including the RIS (Radiology Information System) 130, the image server (PACS) 140, and the HIS (Hospital Information System) 150, the system may be configured so as not to include at least some of them.

Although the case shown in FIG. 1 has exemplified the radiation generation units 114A and 114B and the radiation detectors 115A and 115B, the radiation imaging system 100 may include more combinations of radiation generation units and radiation detectors.

2. Arrangement of Control Apparatus

An example of the arrangement of the control apparatus 110 according to this embodiment will be described next. FIG. 2A is a schematic view showing an example of the hardware arrangement of the control apparatus 110. The control apparatus 110 includes a CPU 201, a RAM 202, a ROM 203, an external memory 204, and a communication I/F unit 205, which are connected to each other via a bus.

The CPU 201 comprehensively controls the operation of the control apparatus 110, and controls each constituent element (the RAM 202 to the communication I/F unit 205) shown in FIG. 2A via the bus.

The RAM 202 functions as a main memory, a work memory, and the like of the CPU 201. When executing processing, the CPU 201 loads a necessary program 2031 and the like from the ROM 203 into the RAM 202 and executes the program 2031 and the like, thereby implementing various types of functional operations. The ROM 203 stores the program 2031 and the like necessary for the execution of processing by the CPU 201. Note that the program 2031 may be stored in the external memory 204.

The external memory 204 stores various types of data, various types of information, and the like necessary for processing executed by the CPU 201 using the program 2031 and the like. The external memory 204 also stores various types of data, various types of information, and the like obtained by, for example, processing executed by the CPU 201 using the program 2031 and the like. The communication I/F unit 205 controls communication with the outside. The bus serves to communicably connect the CPU 201, the RAM 202, the ROM 203, the external memory 204, and the communication I/F unit 205 to each other.

Figure 2B:
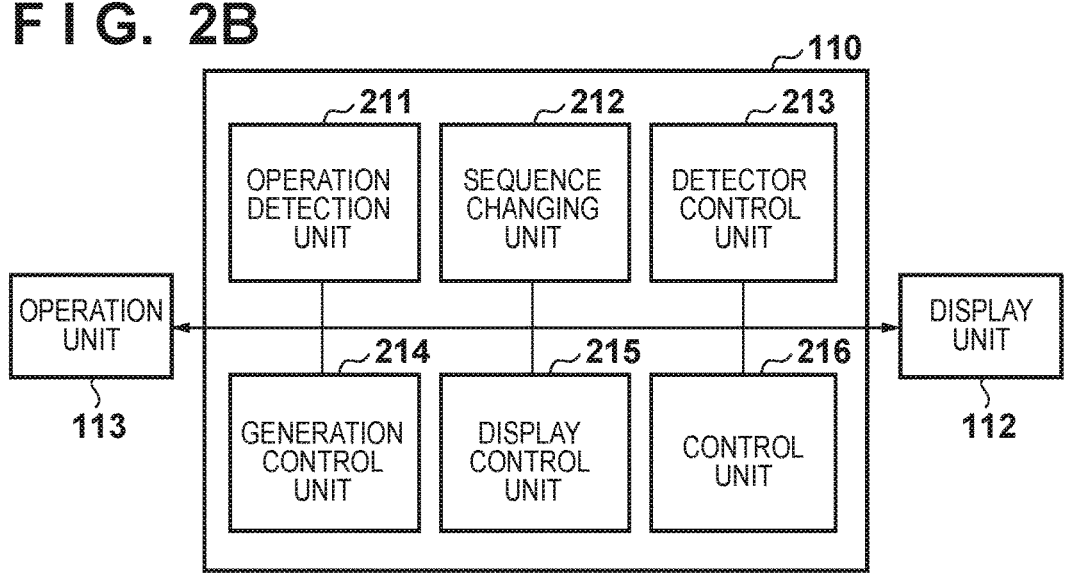
FIG. 2B is a functional block diagram showing the software arrangement of the control apparatus according to the embodiment of the present invention.

FIG. 2B is a functional block diagram showing the software arrangement of the control apparatus 110 according to this embodiment. The control apparatus 110 includes an operation detection unit 211, a sequence changing unit 212, a detector control unit 213, a generation control unit 214, a display control unit 215, and a control unit 216. The CPU 201 implements each function by loading a corresponding program stored in the ROM 203 into the RAM 202 and executing the program.

The operation detection unit 211 detects an operation performed by the user via the operation unit 113. The sequence changing unit 212 changes the sequence of a plurality of pieces of imaging examination information arranged and displayed on the imaging control screen of the display unit 112 according to the imaging sequence based on a user operation detected by the operation detection unit 211. Each piece of imaging examination information includes at least one of the following: an imaging posture (an upright posture, decubitus posture, or the like), an imaging region (a chest region, abdominal region, or the like), an imaging direction (front, side, or the like), the type of radiation detector used for imaging (the radiation detector 115A or 115B or the like), the type of radiation generation unit (the radiation generation unit 114A or 114B or the like), and the like.

The detector control unit 213 controls the operation of the radiation detector 115A or 115B based on the sequence of imaging examination information changed by the sequence changing unit 212. For example, the detector control unit 213 wiredly or wirelessly transmits a control signal to the radiation detector 115A or 115B associated with the leading imaging examination information as an imaging target in accordance with a change in the sequence of imaging examination information. However, imaging examination information as an imaging target is not limited to the leading imaging examination information. The control signal is a signal for instructing an operation in accordance with the contents of imaging examination information as an imaging target. For example, when imaging examination information indicates the use of the radiation detector 115B, the detector control unit 213 sets the radiation detector 115B as a control target. In addition, when imaging examination information indicates an abdominal region as an imaging target, the detector control unit 213 transmits a control signal including an instruction to operate the radiation detector for an accumulation time of radiation three times the accumulation time of radiation when another region is an imaging target. When imaging examination information indicates narrowing down of an irradiation area, the detector control unit 213 transmits a control signal including an instruction to inhibit the operations of pixels, amplifiers, A/D converters, and the like other than an irradiation area. In this manner, the detector control unit 213 executes control on the radiation detector in accordance with imaging examination information whose sequence position is changed based on a user operation. In addition, when the operation of the radiation detector based on the control signal is complete, the detector control unit 213 receives a response signal indicating the completion of a preparation for imaging. The detector control unit 213 also obtains radiation image data obtained by imaging by the radiation detector 115A or 115B.

The generation control unit 214 controls the operation of the radiation generation unit 114A or 114B based on the imaging examination information whose sequence position is changed by the sequence changing unit 212. The generation control unit 214 wiredly or wirelessly transmits a control signal to the radiation generation unit 114A or 114B associated with the leading imaging examination information as an imaging target in accordance with the change in the sequence position of the imaging examination information. The control signal is a signal for instructing an operation in accordance with the imaging examination information as an imaging target. For example, when imaging examination information indicates the use of the radiation generation unit 114B, the generation control unit 214 sets the radiation generation unit 114B as a control target. In addition, the generation control unit 214 may control the irradiation time of radiation based on an imaging target region included in the imaging examination information. When the operation of the radiation generation unit based on the control signal is complete, the generation control unit 214 receives a response signal indicating the completion of a preparation for imaging.

Note that depending on the contents of imaging examination information, no control has already been required on a radiation detector, and control is required on only a radiation generation unit, and vice versa. In such a case, a control signal may be transmitted to only a radiation detector or a radiation generation unit.

The display control unit 215 displays pieces of imaging examination information side by side on the display unit 112, an obtained radiation image on the display unit 112, and display corresponding to an operation performed by the user via the operation unit 113, which is detected by the operation detection unit 211, on the display unit 112. The control unit 216 performs various types of determination and setting while controlling the operation of each processing unit.

In this case, each functional block described above is merely an example, and the control apparatus 110 may be configured so as not to include some of the above function blocks or configured to additionally include functional blocks.

3. Arrangement of Radiation Detector

Figure 2C:
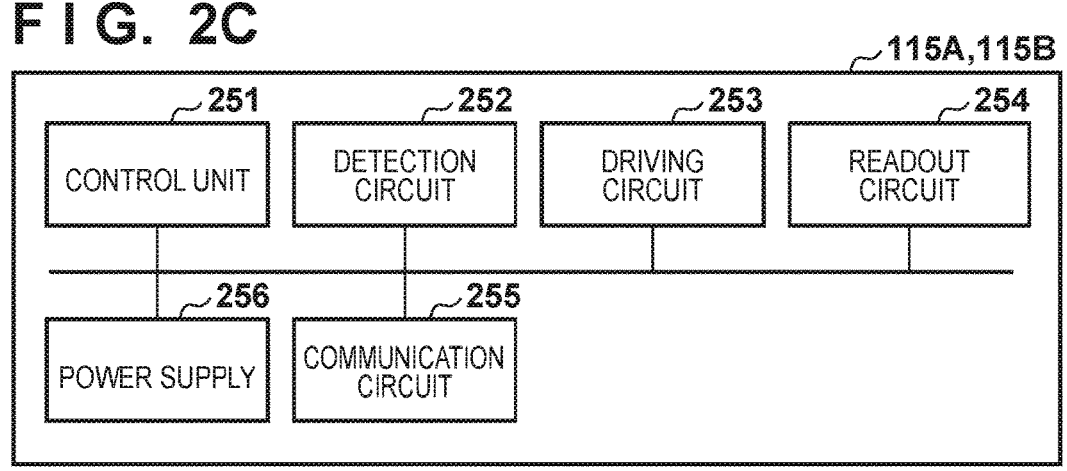
FIG. 2C is a schematic view showing an example of the arrangement of a radiation detector according to the embodiment of the present invention.

An example of the arrangement of each of the radiation detectors 115A and 115B according to this embodiment will be described next. FIG. 2C is a schematic view showing an example of the arrangement of each of the radiation detectors 115A and 115B.

Each of the radiation detectors 115A and 115B includes a control unit 251, a detection circuit 252, a driving circuit 253, a readout circuit 254, a communication circuit 255, and a power supply 256. The control unit 251 comprehensively controls the respective units. The detection circuit 252 monitors outputs from a radiation sensor and detects irradiation with radiation. The driving circuit 253 drives the radiation sensor in an accumulation state or readout state. For example, the control unit 251 issues an instruction to the driving circuit 253 to start an accumulation state based on the detection of irradiation with radiation by the detection circuit 252. The driving circuit 253 drives the radiation sensor in a readout state based on the instruction.

The readout circuit 254 amplifies and A/D-converts a signal read out by the driving circuit 253 to output radiation image data. The communication circuit 255 transmits the radiation image data output from the readout circuit 254, and receives a control signal from the control apparatus 110. The power supply 256 supplies power to each constituent element. The radiation detectors 115A and 115B control operations in accordance with control signals received from the control apparatus 110.

4. Example of Imaging Control Screen

Figure 3A:
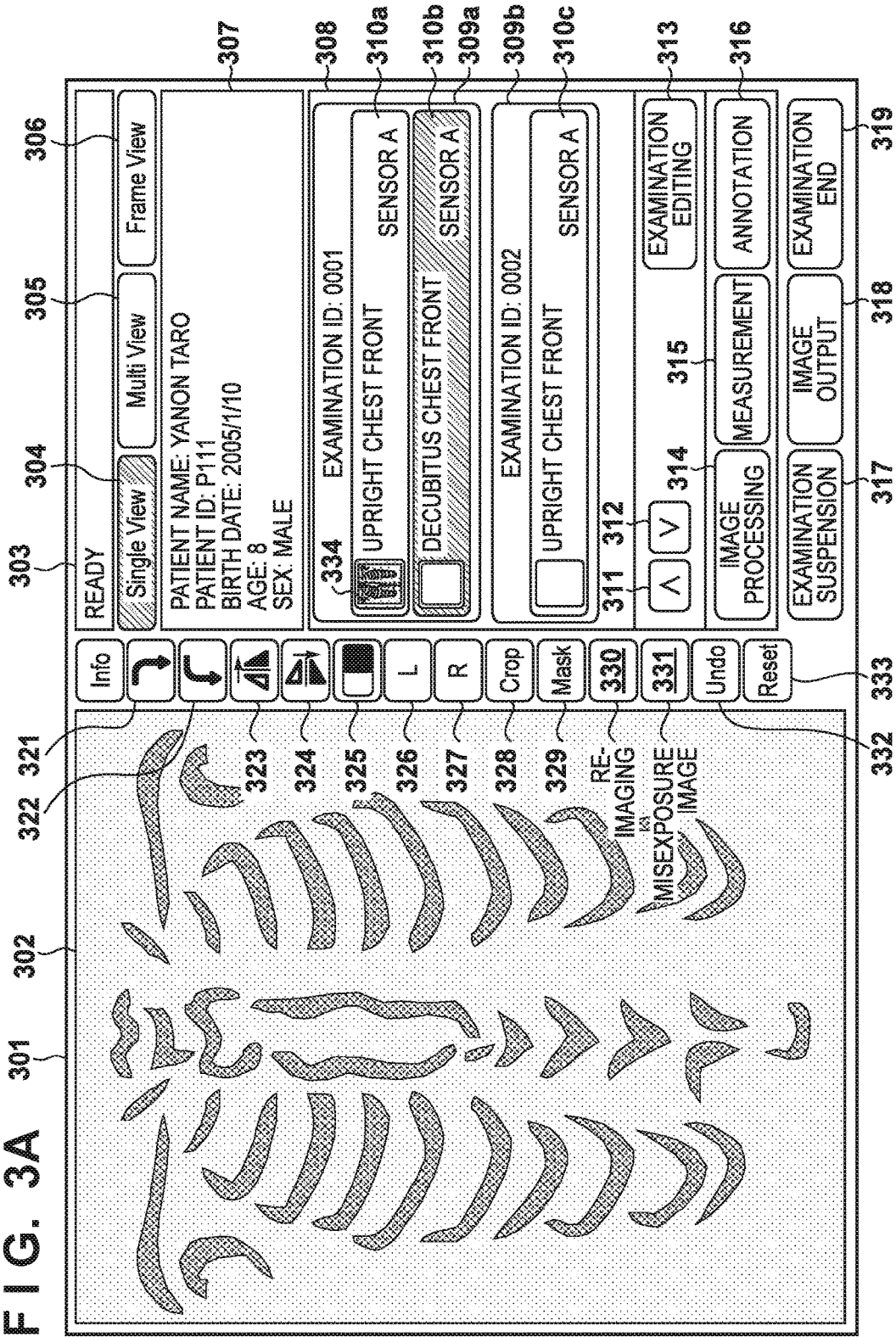
FIG. 3A is a view showing an example of an imaging screen according to the embodiment of the present invention.

FIG. 3A shows an example of an imaging control screen 301 displayed on the display unit 112 according to this embodiment. The imaging control screen 301 includes an image display area 302, a status display area 303, a single view instruction area 304, a multiview instruction area 305, a frame view instruction area 306, a patient information display area 307, an examination display area 308, an examination order display area 309, imaging examination information 310, an imaging examination execution sequence position ascending instruction area 311, an imaging examination execution sequence position descending instruction area 312, an examination editing instruction area 313, an image processing instruction area 314, a measurement instruction area 315, an annotation editing instruction area 316, an examination suspension instruction area 317, an image output instruction area 318, an examination end instruction area 319, a display annotation display switching instruction area 320, a clockwise rotation instruction area 321, a counterclockwise rotation instruction area 322, a lateral inversion instruction area 323, a vertical inversion instruction area 324, a monochrome inversion instruction area 325, an L mark position arrangement instruction area 326, an R mark arrangement instruction area 327, a cutout setting instruction area 328, a mask processing instruction area 329, a re-imaging instruction area 330, a misexposure image instruction area 331, an undo instruction area 332, and a reset instruction area 333.

The image display area 302 displays an obtained radiation image as a preview. When preview selection is switched after imaging, a radiation image selected as a preview is displayed as a preview. In addition, patient information, examination information, irradiation conditions, and the like are displayed as annotations in accordance with settings. Note that in an initial state immediately after the start of examination, no image is displayed.

The status display area 303 is an area where a status notified from the control apparatus 110 or the radiation detector 115A or 115B is displayed in color and character different from those in other areas so as to allow the operator to easily discriminate the status. Upon receiving a status notification from the radiation detector 115A or 115B, the control apparatus 110 determines the display contents in combination with the status, and transmits a status display switching instruction to the display unit 112. If, for example, the radiation generation unit 114A or 114B cannot be used for irradiation with radiation or the radiation detector 115A or 115B cannot be used for radiation detection, "Not Ready (display indicating an imaging preparation state)" is displayed on the sensor status. If the radiation generation unit 114A or 114B can be used for irradiation with radiation and the radiation detector 115A or 115B can be used for radiation detection, "Ready (display indicating an imaging preparation completion state)" is displayed on the sensor status. Note that in this embodiment, the radiation detector 115A is paired with the radiation generation unit 114A, and the radiation detector 115B is paired with the radiation generation unit 114B. For this reason, a sensor status is displayed to indicate the state of a combination of a radiation detector and a radiation generation unit which are to be used for a current examination. In response to the reception of a response signal indicating the completion of a preparation for imaging from a radiation detector and/or a radiation generation unit, the display is changed from "Not Ready" to "Ready".

The single view instruction area 304 is a button for switching to the single view mode of displaying one frame of an image selected as a preview in the image display area 302. When displaying a plurality of frames of images, it is possible to display another frame or play back a moving image by operating the keyboard or mouse during the display of a preview.

The multiview instruction area 305 is a button for switching to the multiview mode of partitioning the image display area 302 into a plurality of display areas in a matrix pattern and displaying images side by side, which are obtained during a currently executed examination. This button is invalid to disable the multiview mode until two or more images are obtained in a currently executed examination.

The frame view instruction area 306 is a button for switching to the frame view mode of partitioning the image display area 302 into a plurality of areas in a matrix pattern and displaying frame images of a moving image selected as a preview side by side. This button is invalid to disable the frame view mode if an image selected as a preview is not a moving image.

The patient information display area 307 is an area where pieces of patient information such as a patient name, patient ID, birth date, age, and sex are displayed. The examination display area 308 is an area where one or a plurality of examination order display areas 309a, 309b, . . . are displayed. The examination order display areas 309a and 309b are areas where pieces of examination information such as examination IDs and examination descriptions are displayed. In addition, imaging examination information selected for an examination is displayed side by side with pieces of imaging examination information 310a, 310b, and 310c and the like.

As the pieces of imaging examination information 310, pieces of imaging examination information such as imaging examination names and the types of radiation detectors are displayed, together with all obtained image thumbnails 334 obtained by executing imaging. In addition, the imaging examination information 310 may include an image thumbnail to be obtained before the execution of imaging or an obtained image thumbnail after the execution of imaging.

The imaging examination execution sequence position ascending instruction area 311 is a button for issuing an instruction to ascend the position of an imaging examination in a scheduled execution sequence. If, for example, the operator presses the imaging examination execution sequence position ascending instruction area 311 while the imaging examination information 310b is selected, the position of the currently selected imaging examination information 310b ascends to the position of the imaging examination information 310a located immediately above it within the same examination so as to replace it. If, however, the leading imaging examination information 310a is selected in the same examination, its position does not ascend.

The imaging examination execution sequence position descending instruction area 312 is a button for issuing an instruction to descend the position of an imaging examination in a scheduled execution sequence. If, for example, the operator presses the imaging examination execution sequence position descending instruction area 312 while the imaging examination information 310a is selected, the position of the currently selected imaging examination information 310a descends to the imaging examination information 310b located immediately below it within the same examination so as to replace it. If, however, the end imaging examination information 310b is selected in the same examination, its position does not descend.

The examination editing instruction area 313 is a button for issuing an instruction to perform examination editing. The image processing instruction area 314 is a button for issuing an instruction to switch between display and non-display of an image processing operation area. The measurement instruction area 315 is a button for issuing an instruction to switch between display and non-display of a measuring operation area. The annotation editing instruction area 316 is a button for issuing an instruction to edit an annotation. The examination suspension instruction area 317 is a button for issuing an instruction to suspend a currently executed examination. The image output instruction area 318 is a button for issuing an instruction to output an obtained image included in a currently executed examination. The examination end instruction area 319 is a button for issuing an instruction to end a currently executed examination.

The clockwise rotation instruction area 321 is a button for clockwise rotating an obtained image currently displayed as a preview. The counterclockwise rotation instruction area 322 is a button for counterclockwise rotating an obtained image currently displayed as a preview. The lateral inversion instruction area 323 is a button for laterally inverting an obtained image currently displayed as a preview. The vertical inversion instruction area 324 is a button for vertically inverting an obtained image currently displayed as a preview. The monochrome inversion instruction area 325 is a button for inverting the Window value of an obtained image currently displayed as a preview.

The L mark arrangement instruction area 326 is a button for arranging the marker "L" on an obtained image currently displayed as a preview. This button can be ON/OFF-switched. The button is switched to ON to arrange "L", and switched to OFF to delete "L". The R mark arrangement instruction area 327 is a button for arranging the marker "R" on an obtained image currently displayed as a preview. This button can be ON/OFF-switched. The button is switched to ON to arrange "R", and switched to OFF to delete "R". The cutout setting instruction area 328 is a button for issuing an instruction to make cutout setting of a region of interest with respect to an obtained image currently displayed as a preview. The mask processing instruction area 329 is a button for issuing an instruction to perform mask processing with respect to an obtained image currently displayed as a preview.

The re-imaging instruction area 330 is a button for issuing an instruction to perform re-imaging with respect to an imaging examination including an image currently selected as a preview. Re-imaging in this case indicates the processing of executing misexposure image processing for an image for which re-imaging is instructed and newly adding the same imaging examination. The misexposure image instruction area 331 is a button for issuing an instruction for a misexposure image with respect to an image currently selected as a preview. Upon executing misexposure image processing, the misexposure image setting included in image information is switched to ON. The undo instruction area 332 is a button for issuing an instruction to perform the undo processing of unwinding, in reverse chronological order, the history of processing for an image currently selected as a preview. The reset instruction area 333 is a button for issuing an instruction to perform the reset processing of discarding all processing for an image currently selected as a preview and returning to a state immediately after imaging.

The user can select/designate each button via the operation unit 113. Alternatively, when the display unit 112 is a touch panel, the user may select/designate each button by directly touching/operating the imaging control screen 301.

5. Example of Examination Display Area

FIGS. 3B-A to 3B-C are schematic views showing the details of the examination display area 308 in FIG. 3A. A mouse cursor 335 can be moved by the operation of the mouse (the operation unit 113) performed by the operator, and allows the operator to perform a drag-and-drop operation with respect to the arbitrary imaging examination information 310 (for example, "decubitus chest front" in FIG. 3B-A). The operation detection unit 211 acquires the position of the mouse cursor 335 which has performed a drag operation. The operation detection unit 211 determines the validity of the drag operation by comparing the moving distance of the mouse cursor 335 by the drag operation with a threshold for the validity of a drag operation.

FIG. 3B-B shows how the imaging examination information 310 is dragged by the mouse cursor 335. The sequence changing unit 212 specifies a movement destination 337 of the imaging examination information 310 based on the position of the mouse cursor 335 during a drag operation and a central position 336 of the imaging examination information. The display control unit 215 displays the mouse cursor 335 and the specified movement destination 337 on the display unit 112.

FIG. 3B-C shows a state after a drop operation in the state shown in FIG. 3B-B. The operation detection unit 211 acquires the position of the mouse cursor 335 which has performed the drop operation. The operation detection unit 211 determines, from the position of the drop operation, whether the drop operation is valid. For example, a valid range of drop operations (for example, the display area of the same examination order) is set in advance, and the operation detection unit 211 performs determination based on the valid range. If the drop operation is valid, the display control unit 215 changes the display sequence position of the imaging examination information 310. In the case shown in FIG. 3B-C, the imaging examination information 310 is moved to the second from the bottom among the respective pieces of imaging examination information with an examination ID of 0001.

Although in the case shown in each of FIGS. 3B-A to 3B-C, the obtained image thumbnail 334 is displayed integrally in the imaging examination information 310, the obtained image thumbnail 334 and the imaging examination information 310 may be separately displayed, as shown in FIG. 3B-D.

6. Display Sequence Changing Processing

Figure 4B:
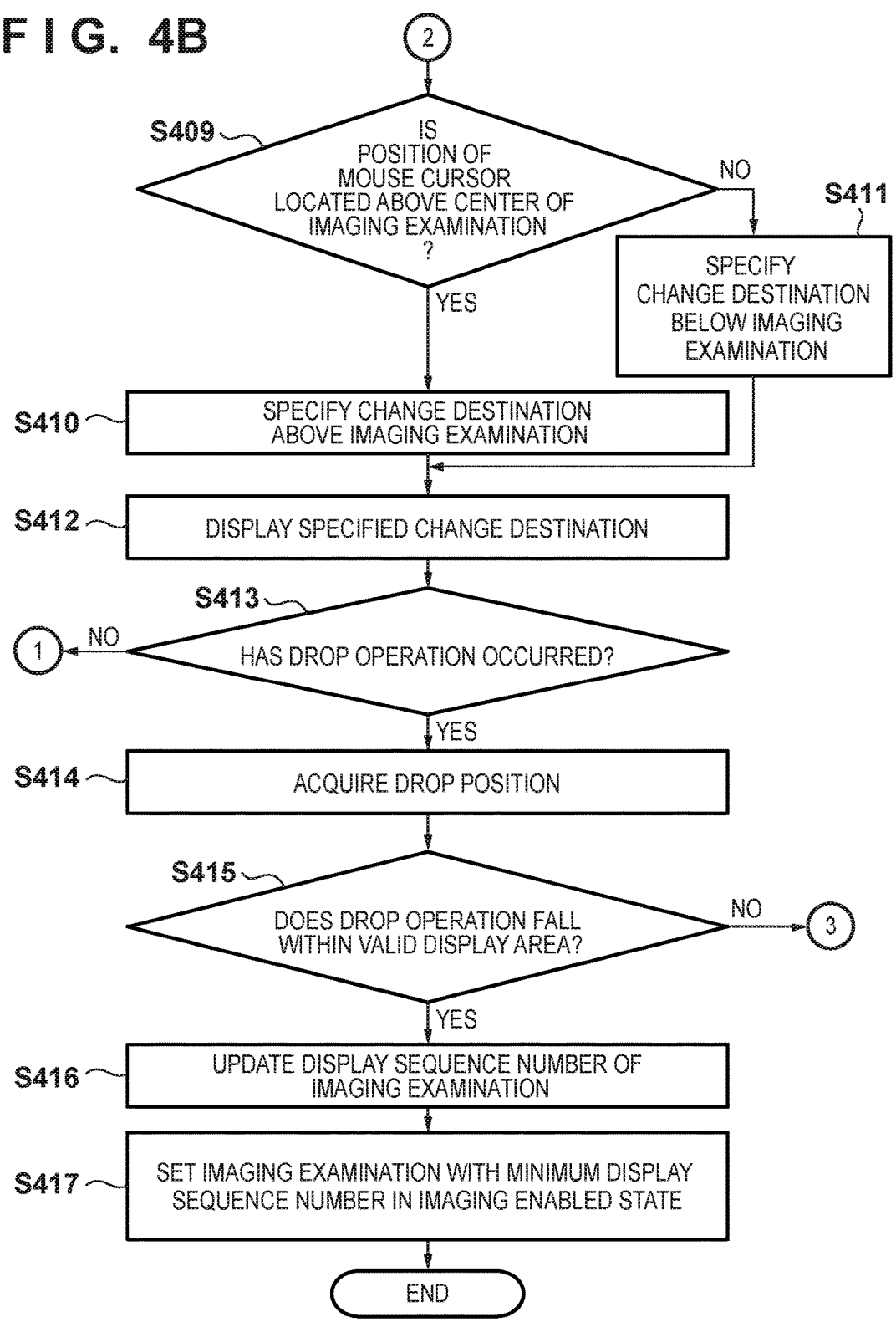

FIGS. 4A and 4B are flowcharts each showing a processing procedure by which the control apparatus 110 according to this embodiment changes the display sequence position of the imaging examination information 310. First of all in step S401, the operation detection unit 211 acquires a signal representing that arbitrary imaging examination information is dragged. In step S402, the operation detection unit 211 acquires the moving distance of the drag operation. In step S403, the control unit 216 determines the validity of the drag operation by comparing the moving distance with a threshold for the validity of a drag operation. If the moving distance is equal to or more than the threshold (YES in step S403), the control unit 216 determines that the drag operation is valid. The process then advances to step S404. If the moving distance is less than the threshold (NO in step S403), the control unit 216 determines that the drag operation is invalid. The process then waits until the moving distance becomes equal to or more than the threshold.

In step S404, the control unit 216 determines, based on information held by the detector control unit 213 and the generation control unit 214, whether an imaging examination list includes an imaging examination in an imaging enabled state. If there is any imaging examination in an imaging enabled state (YES in step S404), the process advances to step S405. If the control unit 216 determines that there is no imaging examination in an imaging enabled state (NO in step S404). The process advances to step S406.

In step S405, the control unit 216 sets the corresponding imaging examination in an imaging disabled state. In step S406, the operation detection unit 211 acquires the position of the mouse cursor 335 during the drag operation.

In step S407, the control unit 216 determines whether the position of the mouse cursor 335 is on an examination order display area (for example, the examination order display area 309a). If the control unit 216 determines that the position is on the examination order display area (YES in step S407), the process advances to step S408. In contrast to this, if the control unit 216 determined that the position is not on the examination order display area (NO in step S407), the process returns to step S406.

In step S408, the control unit 216 acquires the display sequence number of an imaging examination at the position of the mouse cursor 335. In step S409, the control unit 216 determines whether the position of the mouse cursor 335 during the drag operation, which is acquired in step S406, is located above the center of the imaging examination information. If the control unit 216 determines that the position is located above the center of the imaging examination information (YES in step S409), the process advances to step S410. In contrast to this, if the control unit 216 determines that the position is not located above the center of the imaging examination information (NO in step S409), the process advances to step S411.

In step S410, the control unit 216 specifies that the change destination of the display sequence position is located on the imaging examination information at the position of the mouse cursor 335. In step S411, the control unit 216 specifies that the change destination of the display sequence position is located below the imaging examination information at the position of the mouse cursor 335.

In step S412, the display control unit 215 displays the change destination (for example, the movement destination 337) on the display unit 112 in accordance with the specified change destination of the display sequence position.

Subsequently, in step S413, the operation detection unit 211 detects the occurrence of a drop operation. If the operation detection unit 211 has detected the occurrence of a drop operation (YES in step S413), the process advances to step S414. If the operation detection unit 211 has not detected the occurrence of a drop operation (NO in step S413), the process returns to step S406.

In step S414, the operation detection unit 211 acquires the position of the mouse cursor 335 which has performed the drop operation. In step S415, it is determined in step S415 whether the drop operation has been performed within the range of a valid display area. If it is determined that the drop operation has been performed within the valid display area (YES in step S415), the process advances to step 416. If it is determined that the drop operation has been performed in an invalid display area (NO in step S415), the process returns to step 401.

In step S416, the sequence changing unit 212 changes the sequence of the imaging examination information by updating the display sequence number of the imaging examination information. If it is determined that the drop operation has been performed in an invalid display area, the display sequence position of the imaging examination information is not changed.

After the display sequence number of the imaging examination information is updated, the control unit 216 sets the imaging examination information with the minimum display sequence number in an imaging enabled state in step S417. More specifically, the detector control unit 213 transmits a control signal to the radiation detector corresponding to the corresponding imaging examination information, and controls the radiation detector in a state that allows the use of it in accordance with the contents of the imaging examination information. In addition, the generation control unit 214 transmits a control signal to the radiation generation unit associated with the radiation detector corresponding to the imaging examination information, and controls the radiation generation unit in a state that allows the use of it in accordance with the contents of the imaging examination information. The detector control unit 213 and the generation control unit 214 respectively receive signals each indicating an imaging enabled state from the radiation detector and the radiation generation unit. The display control unit 215 changes the display on the status display area 303 from "Not Ready" to "Ready", and changes the background color to a color that can be easily discriminated from that at the time of display of "Not Ready". In addition, as shown in FIG. 3B-D, imaging examination information corresponding to the leading imaging sequence position may be displaced in a display form different from that of the remaining pieces of imaging examination information to facilitate visual recognition of the leading imaging sequence position. With the above operation, each processing in the flowcharts of FIGS. 4A and 4B is terminated.

As described above, the control apparatus (control apparatus 110) according to this embodiment changes the sequence of imaging examination information (for example, the imaging examination information 310) from a plurality of pieces of imaging examination information (for example, the imaging examination information 310) arranged based on an imaging sequence on the imaging control screen (imaging control screen 301) based on a user operation (for example, drag-and-drop operation). Based on the imaging examination information after the change of the sequence, the apparatus controls, for example, a radiation detector (for example, the radiation detector 115A (sensor A)) corresponding to the leading imaging examination information in the imaging sequence to cause the detector to transition to an imaging enabled state.

This allows the user to change a display sequence on the imaging control screen by performing a drag-and-drop operation and can automatically make settings so as to use the leading imaging examination information in the imaging sequence in accordance with the change of the display sequence, thereby improving imaging efficiency and operability.

First Modification

The first modification will exemplify a case in which an image (dragged image) corresponding to imaging examination information during a drag operation is displayed in accordance with the drag operation so as to facilitate visual recognition of how a display sequence is changed. The arrangements of the radiation imaging system, the control apparatus, and the like are the same as those described in the first embodiment.

Figure 5:
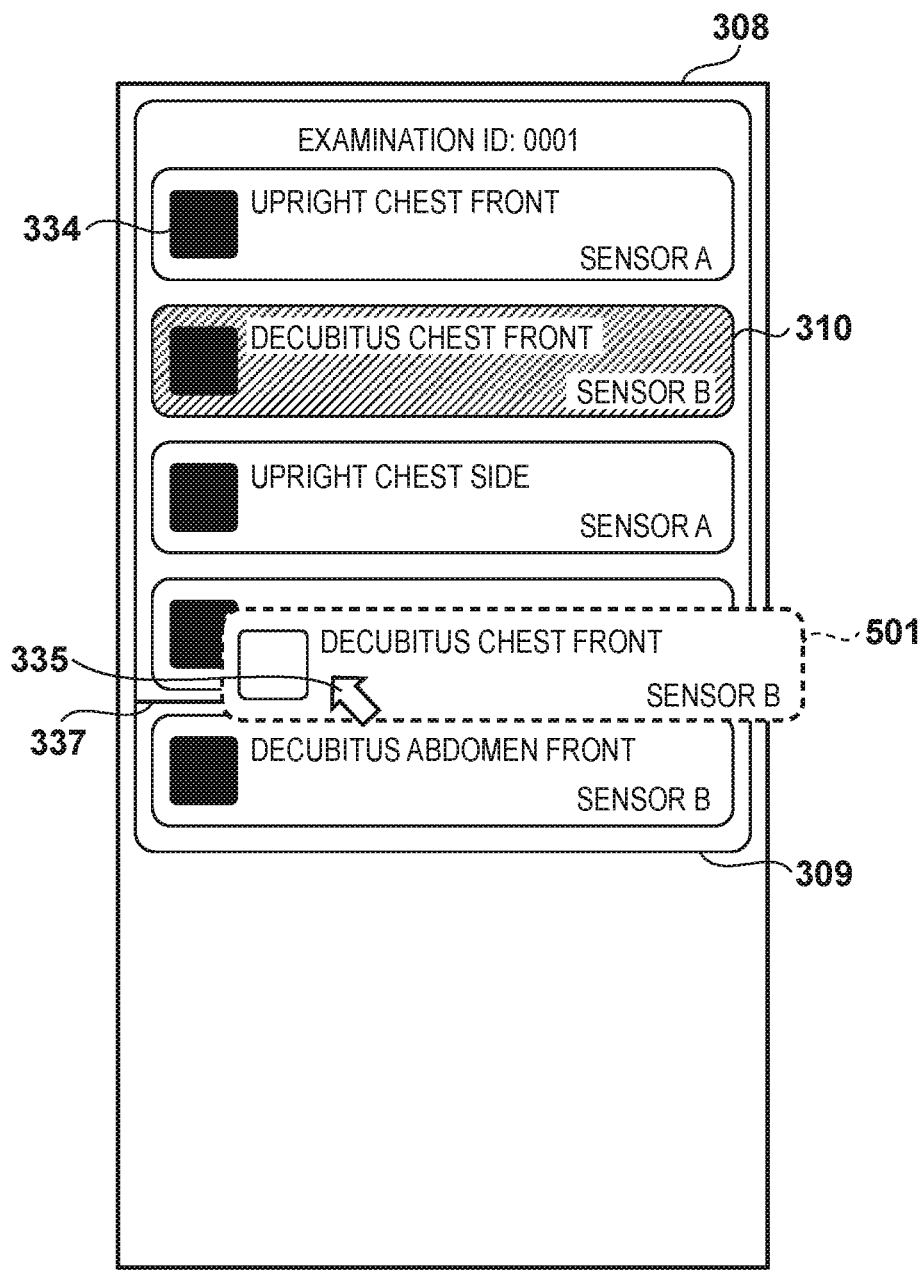
FIG. 5 is a view showing how imaging examination information is dragged by a mouse cursor according to the embodiment of the present invention.

FIG. 5 shows how the imaging examination information 310 is dragged with the mouse cursor 335. A dragged image 501 is an image indicating a target during a drag operation which is set by the display control unit 215. The display control unit 215 may set an arbitrary image (for example, imaging examination information or frame line as a drag target) as an image of the dragged image 501 or set the transmittance of an image to an arbitrary value. In addition, the control unit 216 may set a coordinate position necessary for specifying the change destination of a display sequence position may be set as an arbitrary position of the dragged image 501 instead of the position of the mouse cursor 335 during a drag operation.

FIG. 6 is a flowchart showing a processing procedure by which the control apparatus 110 changes the display sequence position of the imaging examination information 310. The same reference numerals denote the same processing steps as in FIGS. 4A and 4B, and a description of them will be omitted.

If it is determined in step S403 that the drag operation is valid, the process advances to step S601. In step S601, the display control unit 215 displays the set image as the dragged image 501. Subsequently, the process advances to step S404.

As described above, the first modification uses a dragged image indicating a drag target. This provides the effect of facilitating the visual recognition of a change in display sequence.

Second Modification

The second modification will exemplify a case in which the sequence of imaging examination information displayed is rearranged before the execution of a drop operation. The arrangements of the radiation imaging system, the control apparatus, and the like are the same as those described in the first embodiment.

FIGS. 7A to 7D are views each showing how the sequence of imaging examination information is rearranged by dragging the imaging examination information 310 with the mouse cursor 335.

FIG. 7A is a view showing how the imaging examination information 310 is dragged with the mouse cursor 335. The operation detection unit 211 acquires the central positions of pieces of imaging examination information with display sequence positions before and after that of imaging examination information as a drag target or the central position of imaging examination information with either of the display sequence positions. The imaging examination information as the drag target is held in the external memory 204. The control unit 216 sets a center-to-center range 701 from the acquired central positions.

FIG. 7B is a view showing how the imaging examination information 310 as the drag target is hidden. The control unit 216 determines whether the position of the mouse cursor 335 during a drag operation falls outside the center-to-center range 701. If the control unit 216 determines that the position falls outside the range, the display control unit 215 sets the imaging examination information 310 as the drag target in a non-display state.

FIG. 7C is a view showing how the display sequence position of the imaging examination information 310 is changed. The control unit 216 sets the display sequence number of imaging examination information in the change destination range from the hidden imaging examination information 310, and sets a center-to-center range 702 of pieces of imaging examination information before and after the position of the mouse cursor 335 during a drag operation.

FIG. 7D is a view showing how a drop operation is performed from the state shown in FIG. 7C. The control unit 216 determines whether a drop operation has occurred within the center-to-center range 702. In accordance with this determination result, the control unit 216 sets a display sequence number for imaging examination information as a drag target held in the external memory 204.

Figure 8A:
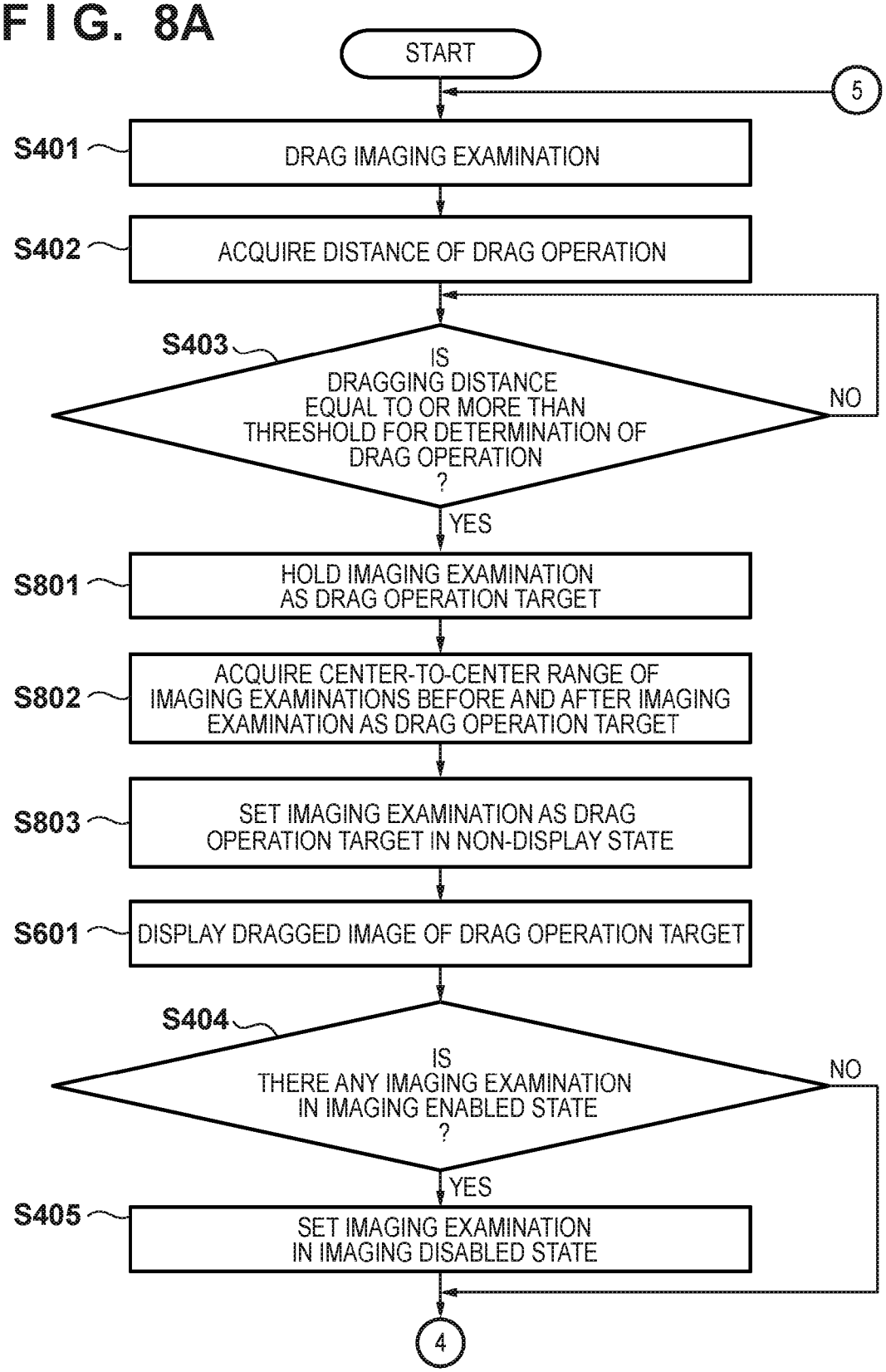
FIGS. 8A to 8C are flowcharts each showing a processing procedure by which the control apparatus according to the embodiment of the present invention changes the display sequence of imaging examination information in accordance with a drag operation before a drop operation.
Figure 8B:
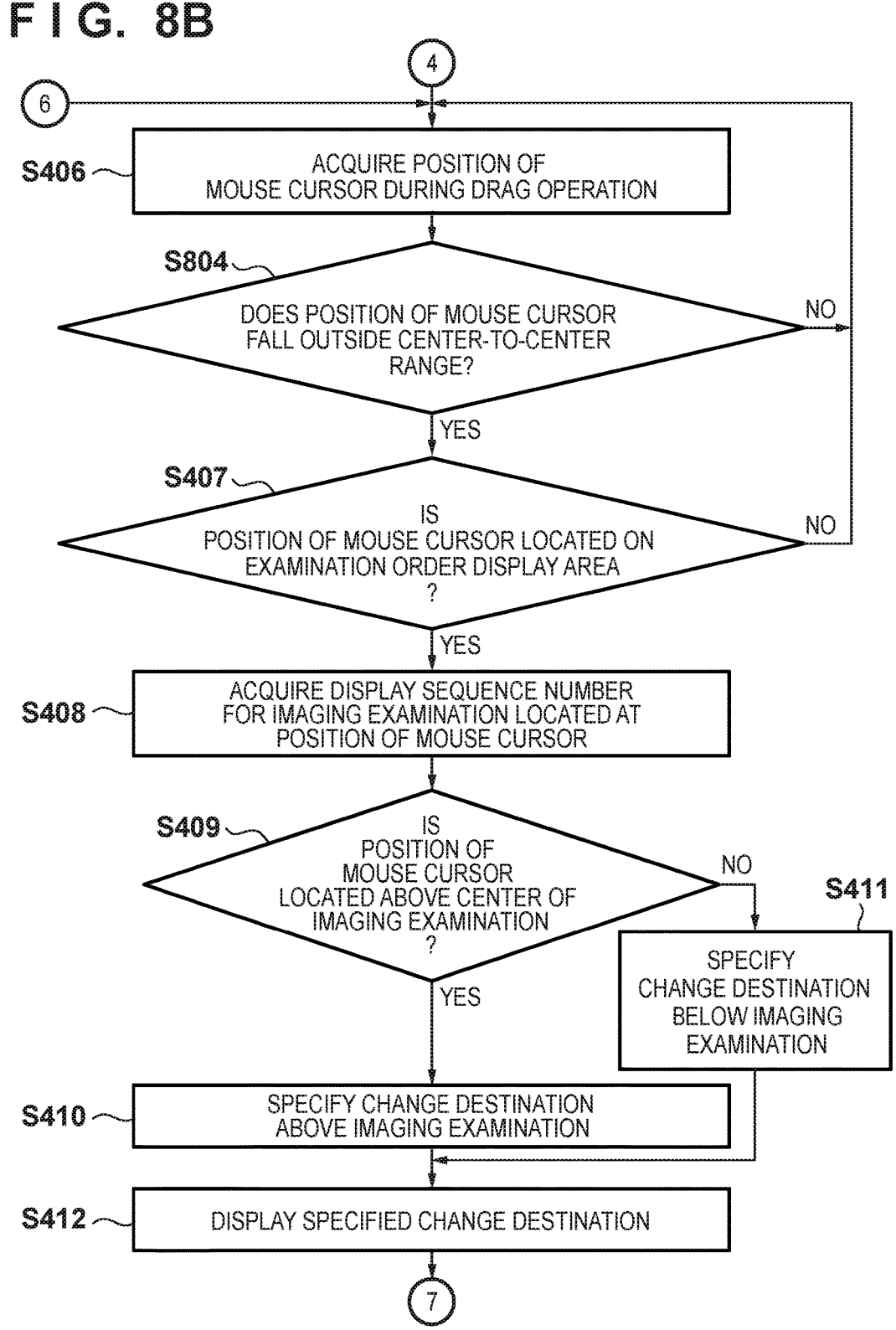
Figure 8C:
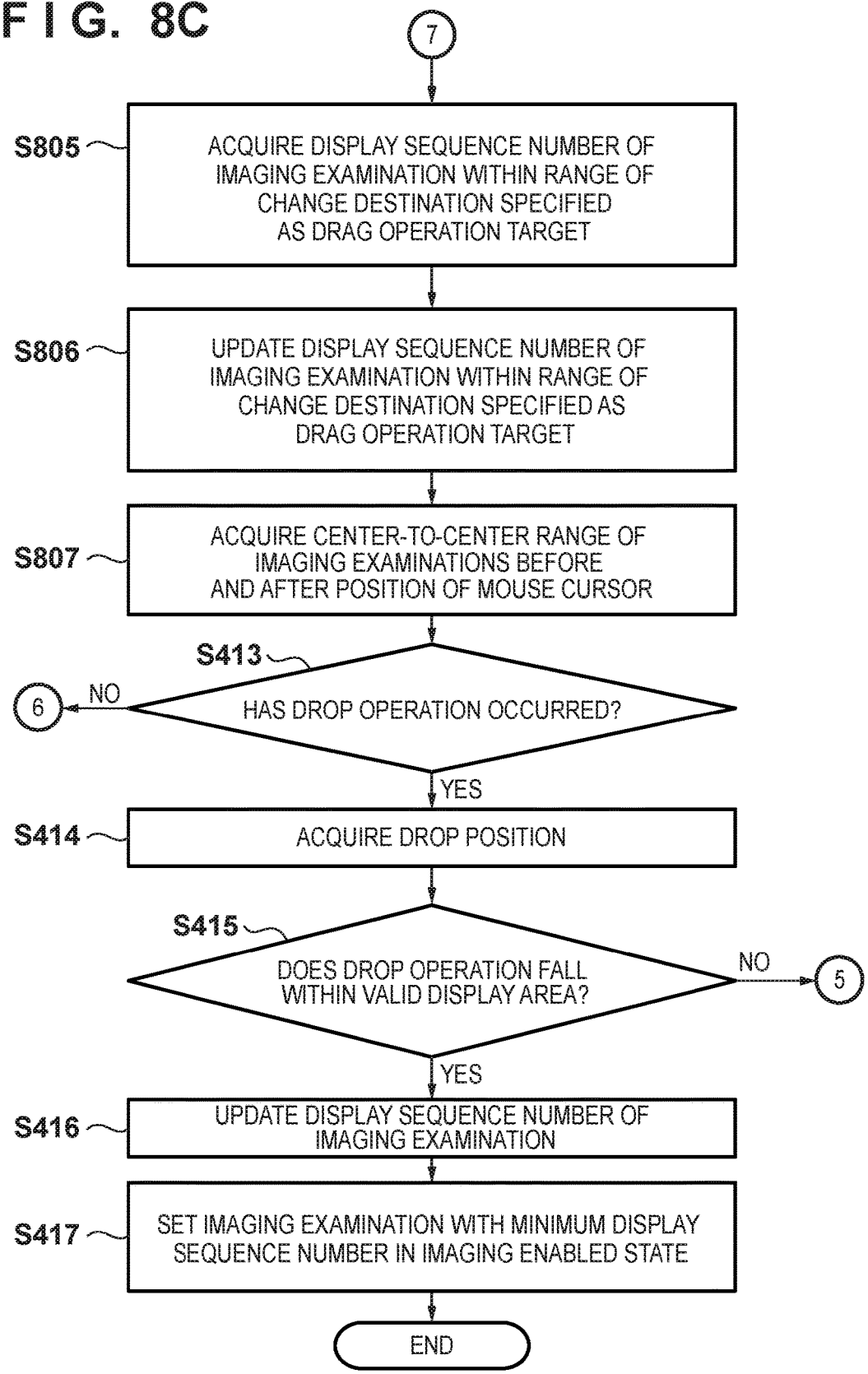

FIGS. 8A to 8C are flowcharts each showing a processing procedure by which the control apparatus 110 changes the display sequence position of the imaging examination information 310 in accordance with a drag operation before a drop operation. The same reference numerals denote the same processing steps as in FIGS. 4A, 4B, and 6, and a description of them will be omitted.

After the processing in step S403, the control unit 216 stores the imaging examination information as the drag target in the external memory 204 in step S801. In step S802, the operation detection unit 211 acquires the central positions of pieces of imaging examination information before and after the imaging examination information as the drag target or the central position of either of the pieces of imaging examination information displayed. The control unit 216 sets a center-to-center range from each acquired central position.

In step S803, the display control unit 215 sets the imaging examination information as the drag operation target in a non-display state. Subsequently, processing in and after step S601 is executed. After processing in step S406, the control unit 216 determines in step S804 whether the position of the mouse cursor 335 during the drag operation falls outside the center-to-center range. If the control unit 216 determines that the position of the mouse cursor 335 falls outside the center-to-center range (YES in step S804), the process advances to step S407. In contrast to this, if the control unit 216 determines that the position of the mouse cursor 335 falls within the center-to-center range 701 (NO in step S804), the process returns to step S406.

After the processing in steps S407 to S412, the control unit 216 acquires the display sequence number of the imaging examination information as the drag operation target and the display sequence number of imaging examination information in the specified change destination range in step S805. In step S806, the control unit 216 updates the display sequence numbers based on the acquired display sequence numbers of the pieces of imaging examination information. In step S807, the control unit 216 acquires the center-to-center range of imaging examination information before and after the position of the mouse cursor 335. Subsequently, processing in and after step S413 is performed.

As has been described above, in the second modification, only moving the position of the mouse cursor by a drag operation will automatically update display sequence numbers. This produces the effect of facilitating visually quickly recognizing how a display sequence is changed.

Third Modification

The first embodiment has exemplified the case in which at least one of a radiation detector and a radiation generation unit which are associated with imaging examination information as an imaging target is controlled based on the sequence of imaging examination information which is changed based on a user operation.

The third modification will exemplify another example of the contents of control on a radiation detector or radiation generation unit.

For example, in accordance with a change in the sequence of imaging examination information, a radiation detector which has being a control target may be set in a power saving state. More specifically, assume that there is an array of a plurality of pieces of imaging examination information for performing imaging by using a plurality of sensors (the first sensor (for imaging, for example, a chest region) having a large size and the second sensor (for imaging, for example, the hand or arm) having a small size) for one patient. In this case, when imaging examination information corresponding to the first sensor is changed from the first position to the second position, it is determined that next imaging is performed by using the second sensor, and control is performed accordingly. At the same time, the first sensor may be set in a power saving state.

Assume that in this case, a power supply state with respect to each radiation detector can take a plurality of states such as a power saving state in which, for example, only a communication circuit and an MPU are activated, a ready state in which a sensor and a driving circuit power supply are turned on, and a readout state in which a readout circuit is turned on.

In addition, a sensor may be activated in accordance with a change in the sequence of imaging examination information. More specifically, assume that three pieces of imaging examination information are arranged in sequence side by side. In this case, when the position of the second imaging examination information is changed to the first position while there is no ready protocol, it may be determined that imaging is started, and the sensor of the radiation detector may be activated.

Second Embodiment

The first embodiment has exemplified the case in which setting is automatically made such that when the user changes a display sequence by a drag-and-drop operation on the imaging control screen, the leading imaging examination information in an imaging sequence can be used in accordance with the change in display sequence.

In contrast to this, the second embodiment will exemplify a case in which a display sequence is automatically changed in accordance with a priority order in rearrangement which is set in advance before imaging. In general, when a large number of pieces of imaging examination information are input to an examination order, it is necessary to search these pieces of information for desired imaging examination information. An examination technician requires much time to manually change a display sequence. In addition, depending on the resolution of a monitor to be used for an examination, the number of pieces of imaging examination information displayed on the imaging control screen is small. This sometimes leads to an increase in time to search for desired imaging examination information. The second embodiment will exemplify a case in which the imaging efficiency is further improved by shortening the time required to search for desired imaging examination information.

The arrangements of the radiation imaging system, the control apparatus, and the like are the same as those described in the first embodiment, and hence a description of them will be omitted.

FIG. 9 is a flowchart showing a processing procedure by which a control apparatus 110 according to the this embodiment automatically changes the display sequence of imaging examination information in accordance with preset priority order items.

Figure 10:
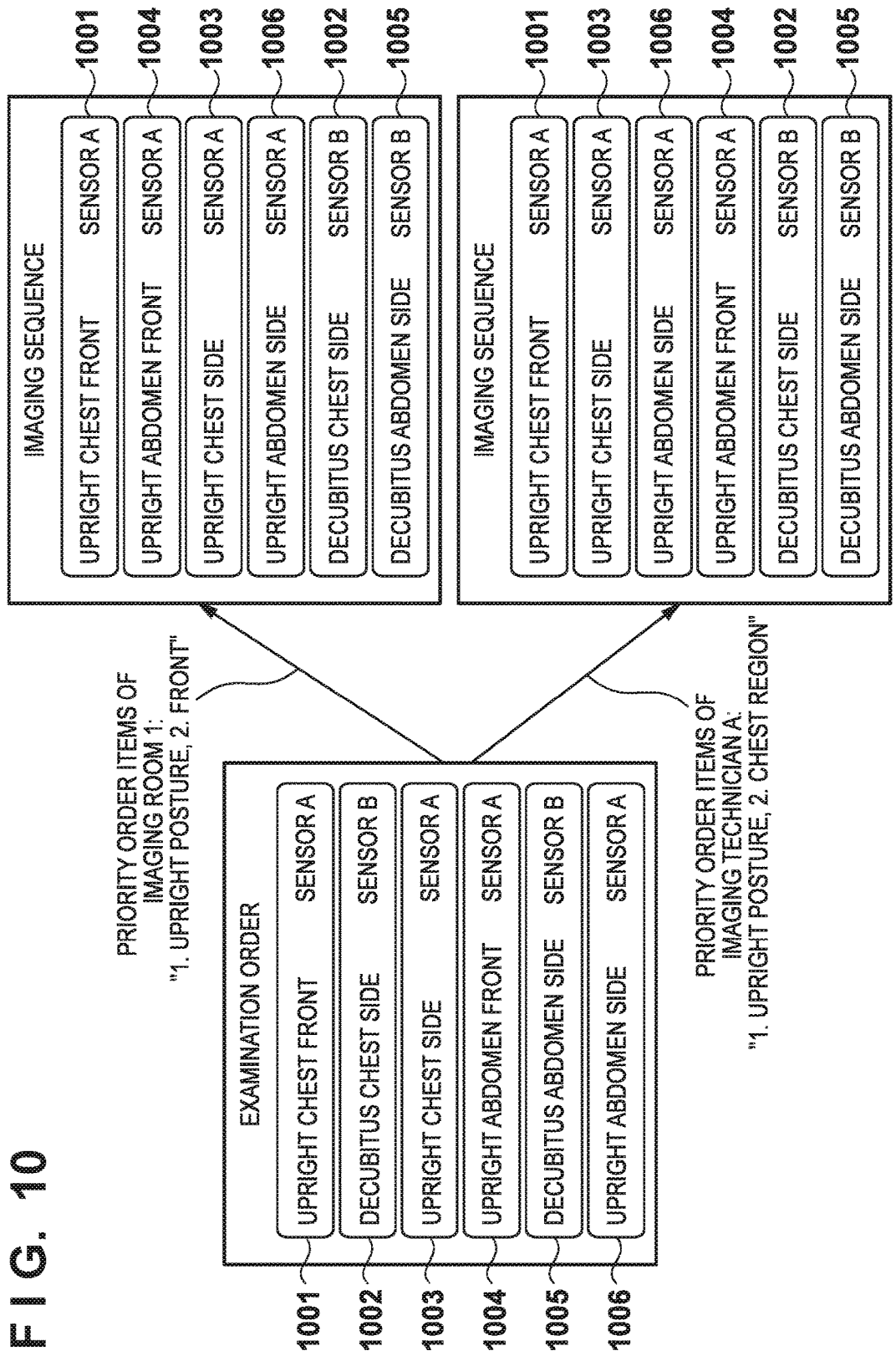
FIG. 10 is a view showing an example of the display sequence of imaging examination information complying with priority order items according to the second embodiment of the present invention.

In step S901, a control unit 216 selects one or more priority order items from a plurality of priority order items for changing a display sequence based on a user operation. A priority order item corresponds to each item in imaging examination information. For example, priority order items include sensors to be used for imaging (radiation detectors 115A and 115B), radiation generation units (radiation generation units 114A and 114B), imaging postures (an upright posture and a decubitus posture), imaging regions (a chest region and an abdominal region), and imaging directions (front and side). One or a plurality of items may be selected from these items. For example, as shown in FIG. 10, as priority order items corresponding to imaging room 1, 1. imaging posture: "upright posture" and 2. imaging direction: "front" may be selected. In addition, imaging technician A may select, as priority order items, 1. imaging posture: "upright posture" and 2. imaging region: "abdominal region". Examination orders in FIG. 10 before the change of the sequence include an array of examination orders 1001 to 1006, the sequence of which will be changed below in accordance with priority order items. Note that priority order items may be set in advance to be used subsequently instead of being selected based on a user operation.

In step S902, imaging starts. In step S903, the control unit 216 determines whether the display sequence has been changed with respect to all the selected priority order items. If the control unit 216 determines that the display sequence position has been changed with respect to all the priority order items (YES in step S902), the processing is terminated. If the display sequence position has not been changed with respect to all the priority order items (NO in step S902), the process advances to step S904.

In step S904, a display control unit 215 rearranges the display sequence according to a priority order item with the highest priority level. In the case of imaging room 1, since "1. imaging posture: upright posture" and "2. imaging direction: front" are selected, the display sequence is rearranged first with reference to "1. upright position". In the case of imaging technician A, since "1. imaging posture: upright posture" and "2. imaging region: abdominal region" are selected, the display sequence is rearranged first with reference to "1. upright position".

In step S905, the display control unit 215 sets a priority order item with the second highest priority level to the highest priority level. In the case of imaging room 1, "2. imaging direction: front" is set to the highest priority level. In the case of imaging technician A, the display control unit 215 sets "2. imaging region: abdominal region" to the highest priority level. Subsequently, the process returns to step S903. In this manner, the processing is continued until the display sequence is changed with respect to all the selected priority order items, thus terminating the series of processing. Note that when rearranging the sequence of imaging examination information, imaging examination information which does not correspond to any of the selected priority order items may be displayed according to an arbitrary display sequence or may be displayed according to the initial sequence position.

As a result, as shown in FIG. 10, in the case of imaging room 1, the imaging sequence is automatically rearranged according to the examination orders 1001, 1004, 1003, 1006, 1002, and 1005. In the case of imaging technician A, the imaging sequence is automatically rearranged according to the examination orders 1001, 1003, 1006, 1004, 1002, and 1005.

As described in the first embodiment, after this change of the sequence, a radiation detector and a radiation generation unit which correspond to the leading imaging examination information in the imaging sequence are controlled to automatically prepare for imaging.

As has been described above, in this embodiment, pieces of imaging examination information are automatically rearranged based on priority order items for imaging which are selected by the user. This makes it possible to shorten the time required to search for desired imaging examination information and further improve the imaging efficiency.

Third Embodiment

The third embodiment will exemplify a case in which a display sequence is automatically changed by comparing an examination order executed in the past with a current examination order. The arrangements of the radiation imaging system, the control apparatus, and the like are the same as those described in the first embodiment, and hence a description of them will be omitted.

Figure 11A:
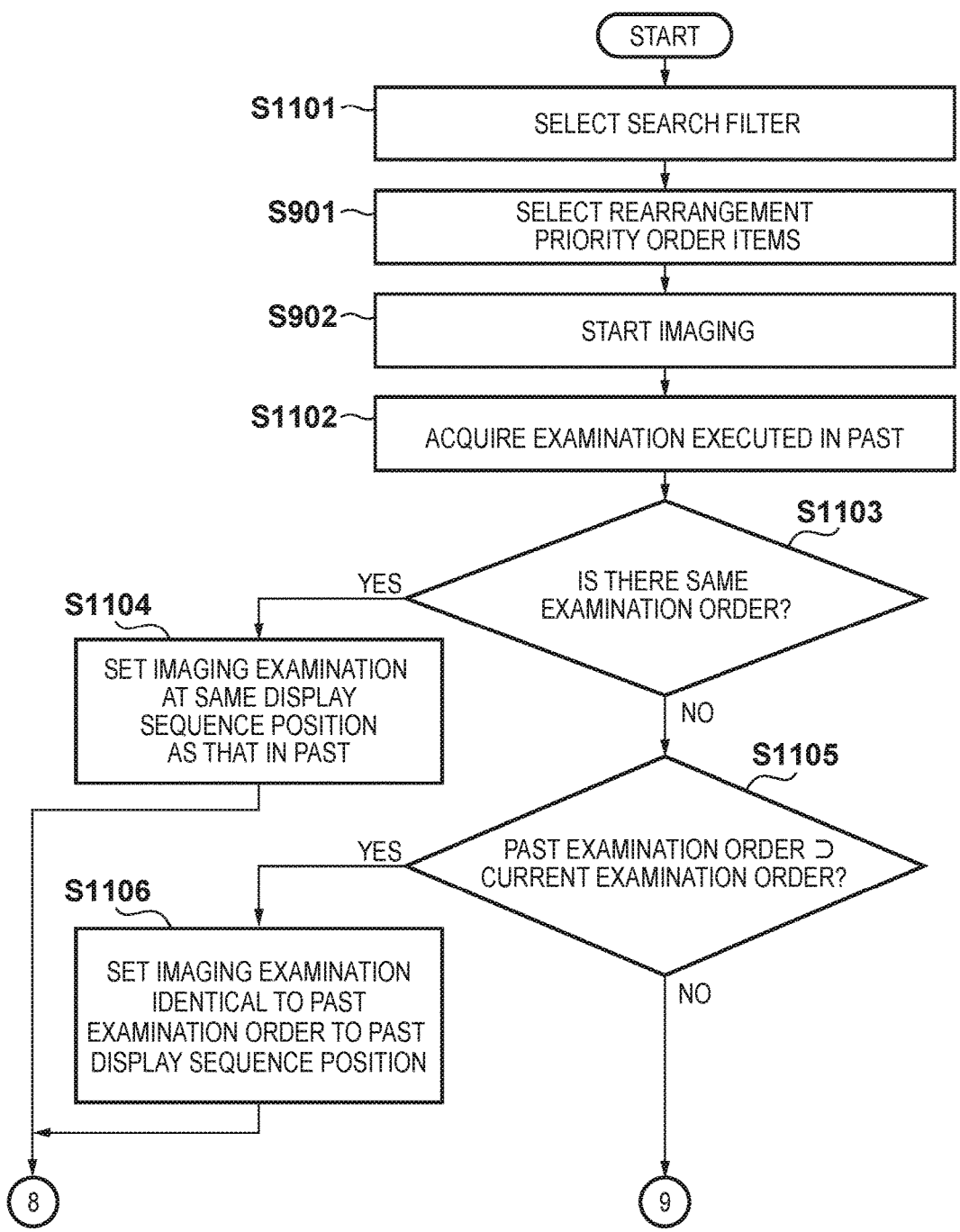
FIGS. 11A and 11B are flowcharts each showing a processing procedure by which a control apparatus according to the third embodiment of the present invention changes the display sequence of imaging examination information based on a past examination order.
Figure 11B:
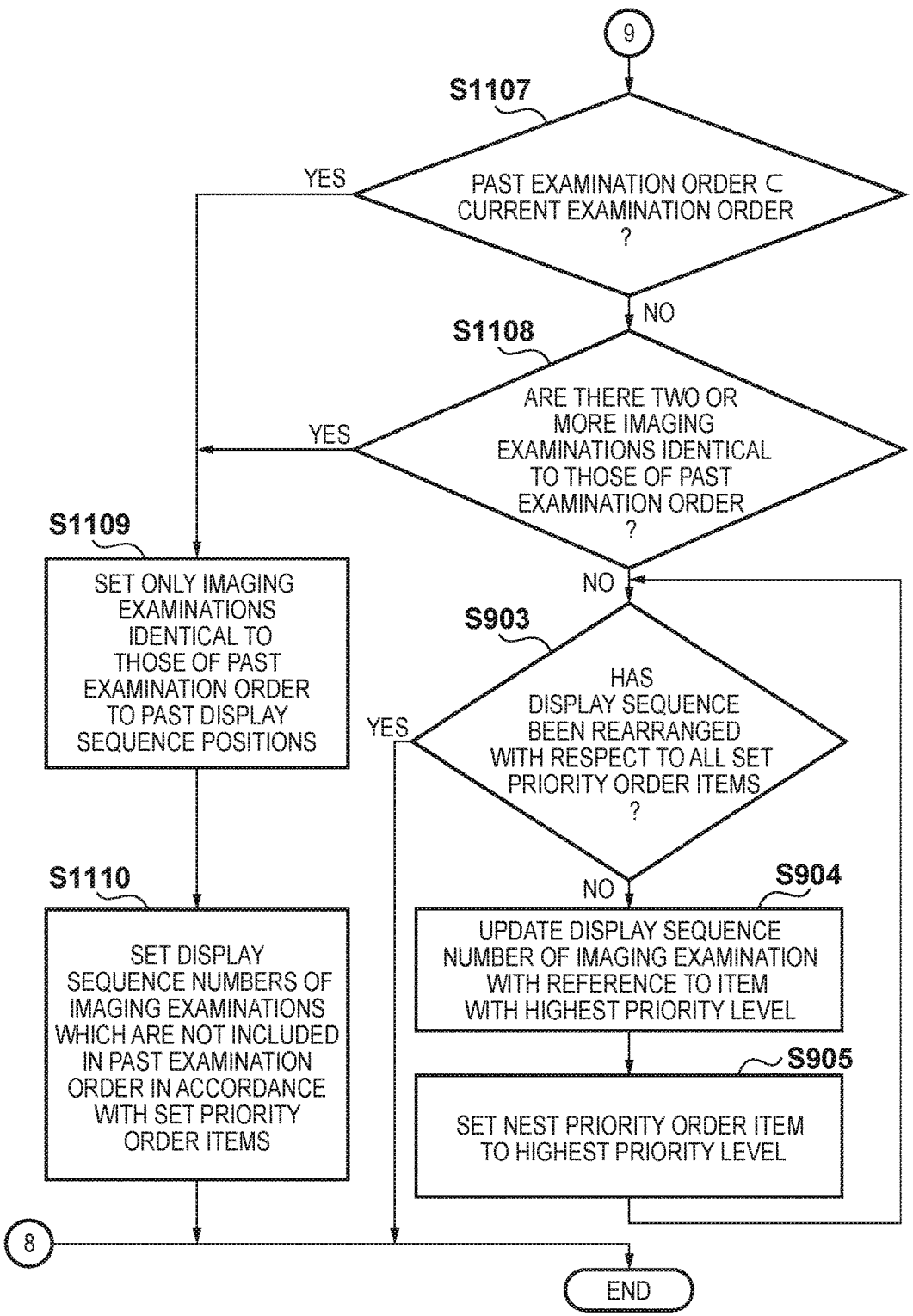

FIGS. 11A and 11B are flowcharts each showing a processing procedure by which a control apparatus 110 according to this embodiment automatically changes the display sequence of imaging examination information based on a past examination order. The same reference numerals denote the same processing steps as in FIG. 9, and a description of them will be omitted.

In step S1101, a control unit 216 selects one or more search filter items from a plurality of preset search filter items based on a user operation. Search filter items are associated with, for example, periods, examination technicians, subjects, and the like. One or a plurality of such items may be selected or may not be selected. Subsequently, the process advances to step S901.

After the processing in step S902, the control unit 216 acquires an examination order corresponding to a search filter item selected from examinations executed in the past in step S1102.

In step S1103, the control unit 216 determines whether the acquired past examination orders include the same examination order as the current examination order. If the control unit 216 determines that there is the same examination order (YES in step S1103), the process advances to step S1104. In contrast to this, if the control unit 216 determines that there is no same examination order (NO in step S1103), the process advances to step S1105.

In step S1104, the control unit 216 sets display sequence numbers to the same display sequence as that of the past examination order with respect to the current examination order, and the processing is terminated.

In step S1105, the control unit 216 determines whether the current examination order is a subset of any of the past examination orders. If the control unit 216 determines that the current examination order is a subset of any of the past examination orders (YES in step S1105), the process advances to step S1106. In contrast to this, if the control unit 216 determines that the current examination order is not a subset of any of the past examination orders (NO in step S1105), the process advances to step S1107.

In step S1106, the control unit 216 sets display sequence numbers for the current examination order such that the same imaging examination information as that of the corresponding past examination order has the same display sequence position.

In step S1107, the control unit 216 determines whether any of the past examination orders is a subset of the current examination order. If the control unit 216 determines that one of the past examination orders is a subset of the current examination order (YES in step S1107), the process advances to step S1109. In contrast to this, if the control unit 216 determines that any of the past examination orders is not a subset of the current examination order (NO in step S1107), the process advances to step S1108.

In step S1108, the control unit 216 determines whether there are two or more pieces of imaging examination information identical to those of a past examination order. If the control unit 216 determines that there are two or more pieces of identical imaging examination information (YES in step S1108), the process advances to step S1009. In contrast to this, if the control unit 216 determines that there are not two or more pieces of identical imaging examination information (YES in step S1108), the process advances to step S903 to perform subsequent processing.

In step S1109, the control unit 216 sets display sequence numbers for the current examination order such that only the imaging examination information identical to those of the past examination order has the same display sequence. In step S1110, the control unit 216 sets display sequence numbers for pieces of imaging examination information which are not included in the past examination order in accordance with preset priority items. The process is then terminated.

As has been described above, this embodiment is configured to automatically change the display sequence of imaging examination information in the current examination order in accordance with priority order items in rearrangement which are set in advance before imaging and/or the comparison between the current examination order and the same or similar past examination order. This makes it possible to reflect the past examination order, and hence can perform imaging in more conformity with the intention of the operator. This can further improve the imaging efficiency.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A control apparatus comprising:
   a changing unit configured to change a sequence of a plurality of imaging examination information, based on a user operation, displayed based on an imaging sequence on an imaging control screen; and
   a control unit configured to control an X-ray detector and an X-ray generation unit which are associated with imaging examination information as an imaging target based on the sequence changed by the changing unit,
   wherein in an imaging enabled state the control unit controls the X-ray detector and the X-ray generation unit, that are associated with the imaging examination information as the imaging target which is set at a leading position in the sequence by the change of the sequence made by the changing unit, and
   causes a display unit to display the X-ray detector by receiving signals indicating the X-ray detector from the X-ray detector.

2. The control apparatus according to claim 1, wherein the control unit transmits a control signal based on the imaging examination information to at least one of an X-ray detector and an X-ray generation unit which are associated with the imaging examination information as the imaging target.

3. The control apparatus according to claim 2, further comprising a display control unit configured to change from display indicating an imaging preparation state to display indicating an imaging enabled state in which an imaging preparation has been completed based on reception of a response signal corresponding to the control signal.

4. The control apparatus according to claim 3, wherein the display control unit displays the display indicating the imaging enabled state in a display form different from the display indicating the imaging preparation state.

5. The control apparatus according to claim 1, further comprising a display control unit configured to display the imaging examination information as the imaging target in a display format different from imaging examination information.

6. The control apparatus according to claim 1, wherein the changing unit specifies a movement destination of imaging examination information based on the drag operation when the user operation is a drag operation of dragging the imaging examination information on the imaging control screen.

7. The control apparatus according to claim 6, wherein the changing unit sets a number indicating a display sequence position of imaging examination information in accordance with the specified movement destination.

8. The control apparatus according to claim 1, wherein the changing unit specifies a movement destination of imaging examination information based on the operation of dragging and dropping when the user operation is an operation of dragging and dropping the imaging examination information.

9. The control apparatus according to claim 1, further comprising a display control unit configured to move and display an image corresponding to the imaging examination information on the imaging control screen in accordance with a drag operation when the user operation is an operation of dragging the imaging examination information on the imaging control screen.

10. The control apparatus according to claim 1, wherein the imaging examination information includes an imaging posture, an imaging region, an imaging direction, and a type of X-ray detector or X-ray generation unit which is used for imaging.

11. An operation method for a control apparatus, the operation method comprising:
changing a sequence of a plurality of imaging examination information, based on a user operation, displayed based on an imaging sequence on an imaging control screen; and
controlling an X-ray detector and a X-ray generation unit which are associated with imaging examination information as an imaging target based on the sequence changed in the changing, wherein in an imaging enabled state
the X-ray detector and the X-ray generation unit, that are associated with the imaging examination information as the imaging target which is set at a leading position in the sequence by the change of the sequence made in the changing, are controlled, and
a display unit is caused to display the X-ray detector by receiving signals indicating the X-ray detector from the X-ray detector.

12. A non-transitory computer-readable storage medium storing a computer program for causing a computer to execute each step in an operation method for a control apparatus, the operation method comprising:
changing a sequence of a plurality of imaging examination information, based on a user operation, displayed based on an imaging sequence on an imaging control screen; and
controlling an X-ray detector and a X-ray generation unit which are associated with imaging examination information as an imaging target based on the sequence changed in the changing, wherein in an imaging enabled state
the X-ray detector and the X-ray generation unit, which are associated with the imaging examination information as the imaging target which is set at a leading position in the sequence by the change of the sequence made in the changing, are controlled, and
a display unit is caused to display the X-ray detector by receiving signals indicating the X-ray detector from the X-ray detector.

13. A control apparatus comprising:
a changing unit configured to change a sequence of a plurality of imaging examination information, based on a user operation, displayed based on an imaging sequence on an imaging control screen; and
a control unit configured to control an X-ray detector and a X-ray generation unit which are associated with imaging examination information as an imaging target based on the sequence changed by the changing unit, wherein in an imaging enabled state the control unit
controls the X-ray detector, that is associated with the imaging examination information as the imaging target that is set at a leading position in the sequence by the change of the sequence made by the changing unit, and an irradiation condition of the X-ray generation unit that is associated with the imaging examination information as the imaging target which is set at the leading position in the sequence, and
causes a display unit to display the X-ray detector by receiving signals indicating the X-ray detector from the X-ray detector.

14. An operation method for a control apparatus, the operation method comprising:
changing a sequence of a plurality of imaging examination information, based on a user operation, displayed based on an imaging sequence on an imaging control screen; and
controlling an X-ray detector and a X-ray generation unit which are associated with imaging examination information as an imaging target based on the sequence changed in the changing, wherein in an imaging enabled state
the X-ray detector, that is associated with the imaging examination information as the imaging target which is set at a leading position in the sequence by the change of the sequence made by the changing unit, is controlled, and an irradiation condition of the X-ray generation unit that is associated with the imaging examination information as the imaging target which is set at the leading position in the sequence is controlled, and
a display unit is caused to display the X-ray detector by receiving signals indicating the X-ray detector in the imaging enabled state from the X-ray detector.

15. A non-transitory computer-readable storage medium storing a computer program for causing a computer to execute each step in an operation method for a control apparatus, the operation method comprising:
changing a sequence of a plurality of imaging examination information, based on a user operation, displayed based on an imaging sequence on an imaging control screen; and
controlling an X-ray detector and a X-ray generation unit which are associated with imaging examination information as an imaging target based on the sequence changed in the changing, wherein in an imaging enabled state the X-ray detector, that is associated with the imaging examination information as the imaging target which is set at a leading position in the sequence by the change of the sequence made by the changing unit, is controlled, and an irradiation condition of the X-ray generation unit that is associated with the imaging examination information as the imaging target which is set at the leading position in the sequence is controlled, and a display unit is caused to display the X-ray detector by receiving signals indicating the X-ray detector in the imaging enabled state from the X-ray detector.

\* \* \* \* \*